(12) United States Patent
Williams et al.

(10) Patent No.: US 11,931,039 B2
(45) Date of Patent: Mar. 19, 2024

(54) SURGICAL BUTTRESS LOADING AND ATTACHING/DETACHING ASSEMBLIES

(71) Applicant: Covidien LP, Mansfield, MA (US)

(72) Inventors: Justin Williams, Southbury, CT (US); Stanislaw Marczyk, Stratford, CT (US); Russell Pribanic, Roxbury, CT (US); Suresh Kumar Prema Mohanasundaram, Chennai (IN); Rajesh Palakunnath, Hyderabad (IN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/705,437

(22) Filed: Mar. 28, 2022

(65) Prior Publication Data
US 2022/0211376 A1     Jul. 7, 2022

Related U.S. Application Data

(63) Continuation of application No. 16/387,951, filed on Apr. 18, 2019, now Pat. No. 11,284,896.
(Continued)

(51) Int. Cl.
| | | |
|---|---|---|
| *A61B 17/072* | (2006.01) | |
| *A61B 17/115* | (2006.01) | |
| *A61B 17/00* | (2006.01) | |

(52) U.S. Cl.
CPC .... *A61B 17/07292* (2013.01); *A61B 17/1155* (2013.01); *A61B 2017/00424* (2013.01);
(Continued)

(58) Field of Classification Search
CPC . A61B 17/07292; B65H 49/205; B65H 75/14
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| | (Continued) | |

FOREIGN PATENT DOCUMENTS

| | | |
|---|---|---|
| CA | 2282761 A1 | 9/1998 |
| CN | 101507636 A | 8/2009 |
| | (Continued) | |

OTHER PUBLICATIONS

Extended European Search Report corresponding to EP 13 15 6297.7, completed Jun. 4, 2013 and dated Jun. 13, 2013; (7 pp).
(Continued)

*Primary Examiner* — Thanh K Truong
*Assistant Examiner* — Patrick B Fry
(74) *Attorney, Agent, or Firm* — Carter, DeLuca & Farrell LLP

(57) ABSTRACT

A surgical stapling system includes a surgical stapling apparatus and a staple cartridge surgical buttress assembly. The surgical stapling apparatus includes a handle assembly, an elongate tubular body extending distally from the handle assembly, and an end effector extending distally from the elongate tubular body. The end effector includes an anvil assembly and a staple cartridge assembly. The staple cartridge surgical buttress assembly includes a surgical buttress and a leash. The surgical buttress includes a body having an annular configuration and legs extending from the body. The body is positioned against a tissue facing surface of the staple cartridge assembly and the legs are positioned against a housing of the staple cartridge assembly. The leash is threaded through at least one of the legs and extends proximally from the surgical buttress towards the handle assembly.

20 Claims, 17 Drawing Sheets

Related U.S. Application Data

(60) Provisional application No. 62/789,580, filed on Jan. 8, 2019, provisional application No. 62/725,327, filed on Aug. 31, 2018, provisional application No. 62/668,851, filed on May 9, 2018, provisional application No. 62/668,858, filed on May 9, 2018.

(52) U.S. Cl.
CPC ............... *A61B 2017/00477* (2013.01); *A61B 2017/07257* (2013.01); *A61B 2017/07271* (2013.01)

(56) References Cited

U.S. PATENT DOCUMENTS

| | | | |
|---|---|---|---|
| 3,364,200 A | 1/1968 | Ashton et al. | |
| 3,499,591 A | 3/1970 | Green | |
| 3,797,494 A | 3/1974 | Zaffaroni | |
| 3,939,068 A | 2/1976 | Wendt et al. | |
| 3,948,666 A | 4/1976 | Kitanishi et al. | |
| 4,064,062 A | 12/1977 | Yurko | |
| 4,166,800 A | 9/1979 | Fong | |
| 4,282,236 A | 8/1981 | Broom | |
| 4,347,847 A | 9/1982 | Usher | |
| 4,354,628 A | 10/1982 | Green | |
| 4,416,698 A | 11/1983 | McCorsley, III | |
| 4,429,695 A | 2/1984 | Green | |
| 4,452,245 A | 6/1984 | Usher | |
| 4,473,077 A | 9/1984 | Noiles et al. | |
| 4,576,167 A | 3/1986 | Noiles | |
| 4,605,730 A | 8/1986 | Shalaby et al. | |
| 4,626,253 A | 12/1986 | Broadnax, Jr. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,005,749 A | 4/1991 | Aranyi | |
| 5,014,899 A | 5/1991 | Presty et al. | |
| 5,040,715 A | 8/1991 | Green et al. | |
| 5,057,334 A | 10/1991 | Vail | |
| 5,065,929 A | 11/1991 | Schulze et al. | |
| 5,112,496 A | 5/1992 | Dhawan et al. | |
| 5,119,983 A | 6/1992 | Green et al. | |
| 5,162,430 A | 11/1992 | Rhee et al. | |
| 5,205,459 A | 4/1993 | Brinkerhoff et al. | |
| 5,263,629 A | 11/1993 | Trumbull et al. | |
| 5,281,197 A | 1/1994 | Arias et al. | |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,324,775 A | 6/1994 | Rhee et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,405,072 A | 4/1995 | Zlock et al. | |
| 5,410,016 A | 4/1995 | Hubbell et al. | |
| 5,425,745 A | 6/1995 | Green et al. | |
| 5,441,193 A | 8/1995 | Gravener | |
| 5,441,507 A | 8/1995 | Wilk | |
| 5,443,198 A | 8/1995 | Viola et al. | |
| 5,468,253 A | 11/1995 | Bezwada et al. | |
| 5,484,913 A | 1/1996 | Stilwell et al. | |
| 5,489,308 A | 2/1996 | Kuslich | |
| 5,503,638 A | 4/1996 | Cooper et al. | |
| 5,514,379 A | 5/1996 | Weissleder et al. | |
| 5,542,594 A | 8/1996 | McKean et al. | |
| 5,543,441 A | 8/1996 | Rhee et al. | |
| 5,549,628 A | 8/1996 | Cooper et al. | |
| 5,550,187 A | 8/1996 | Rhee et al. | |
| 5,575,803 A | 11/1996 | Cooper et al. | |
| 5,588,579 A | 12/1996 | Schnut et al. | |
| 5,645,915 A | 7/1997 | Kranzler et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,752,974 A | 5/1998 | Rhee et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,819,350 A | 10/1998 | Wang | |
| 5,833,695 A | 11/1998 | Yoon | |
| 5,843,096 A | 12/1998 | Igaki et al. | |
| 5,871,135 A | 2/1999 | Williamson, IV et al. | |
| 5,874,500 A | 2/1999 | Rhee et al. | |
| 5,895,412 A | 4/1999 | Tucker | |
| 5,895,415 A | 4/1999 | Chow et al. | |
| 5,902,312 A * | 5/1999 | Frater | A61B 17/07207 606/148 |
| 5,908,427 A | 6/1999 | McKean et al. | |
| 5,915,616 A | 6/1999 | Viola et al. | |
| 5,931,847 A | 8/1999 | Bittner et al. | |
| 5,957,363 A | 9/1999 | Heck | |
| 5,964,394 A | 10/1999 | Robertson | |
| 5,964,774 A | 10/1999 | McKean et al. | |
| 5,997,895 A | 12/1999 | Narotam et al. | |
| 6,019,791 A | 2/2000 | Wood | |
| 6,027,068 A * | 2/2000 | Lantsman | B65H 49/205 226/193 |
| 6,030,392 A | 2/2000 | Dakov | |
| 6,032,849 A | 3/2000 | Mastri et al. | |
| 6,045,560 A | 4/2000 | McKean et al. | |
| 6,053,390 A | 4/2000 | Green et al. | |
| 6,063,097 A | 5/2000 | Oi et al. | |
| 6,080,169 A | 6/2000 | Turtel | |
| 6,093,557 A | 7/2000 | Pui et al. | |
| 6,099,551 A | 8/2000 | Gabbay | |
| 6,125,574 A | 10/2000 | Ganaja | |
| 6,142,933 A | 11/2000 | Longo et al. | |
| 6,149,667 A | 11/2000 | Hovland et al. | |
| 6,152,943 A | 11/2000 | Sawhney | |
| 6,155,265 A | 12/2000 | Hammerslag | |
| 6,156,677 A | 12/2000 | Brown Reed et al. | |
| 6,165,201 A | 12/2000 | Sawhney et al. | |
| 6,179,862 B1 | 1/2001 | Sawhney | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,270,530 B1 | 8/2001 | Eldridge et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,309,569 B1 | 10/2001 | Farrar et al. | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,330,965 B1 | 12/2001 | Milliman et al. | |
| 6,399,362 B1 | 6/2002 | Pui et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,500,777 B1 | 12/2002 | Wiseman et al. | |
| 6,503,257 B2 | 1/2003 | Grant et al. | |
| 6,514,283 B2 | 2/2003 | DiMatteo et al. | |
| 6,514,534 B1 | 2/2003 | Sawhney | |
| 6,517,566 B1 | 2/2003 | Hovland et al. | |
| 6,551,356 B2 | 4/2003 | Rousseau | |
| 6,566,406 B1 | 5/2003 | Pathak et al. | |
| 6,568,398 B2 | 5/2003 | Cohen | |
| 6,590,095 B1 | 7/2003 | Schleicher et al. | |
| 6,592,597 B2 | 7/2003 | Grant et al. | |
| 6,605,294 B2 | 8/2003 | Sawhney | |

(56) References Cited

U.S. PATENT DOCUMENTS

| | | | |
|---|---|---|---|
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2* | 12/2003 | Grant ............... A61B 17/07207 |
| | | | 606/220 |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,052,699 B1 | 11/2011 | Sherwinter |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,256,656 B2 | 9/2012 | Milliman et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |

(56) References Cited

U.S. PATENT DOCUMENTS

| | | |
|---|---|---|
| 8,348,130 B2 | 1/2013 | Shah et al. |
| 8,353,438 B2 * | 1/2013 | Baxter, III ......... A61B 1/00087 |
| | | 606/1 |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | Mckay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,899,466 B2 * | 12/2014 | Baxter, III ............. A61B 46/10 |
| | | 227/179.1 |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 * | 2/2015 | Shah ................ A61B 17/07207 |
| | | 606/220 |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,895,151 B2 | 2/2018 | Milliman |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 10,435,268 B2 * | 10/2019 | Briggs ................. B65H 49/205 |
| 10,932,784 B2 | 3/2021 | Mozdzierz et al. |
| 11,272,927 B2 * | 3/2022 | Swayze ............. A61B 17/1155 |
| 11,284,896 B2 | 3/2022 | Williams et al. |

(56) References Cited

U.S. PATENT DOCUMENTS

| | | |
|---|---|---|
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | De La Torre et al. |
| 2007/0203510 A1 | 8/2007 | Bettuchi |
| 2007/0243227 A1 | 10/2007 | Gertner |
| 2007/0246505 A1* | 10/2007 | Pace-Floridia ....... A61L 31/048 227/175.1 |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0012641 A1 | 1/2012 | Milliman et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153634 A1 | 6/2013 | Carter et al. |
| 2013/0153636 A1 | 6/2013 | Shelton, IV et al. |
| 2013/0153641 A1 | 6/2013 | Shelton, IV et al. |
| 2013/0193190 A1 | 8/2013 | Carter et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0217148 A1 | 8/2014 | Penna |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157320 A1 | 6/2015 | Zergiebel et al. |
| 2015/0157321 A1 | 6/2015 | Zergiebel et al. |
| 2015/0201939 A1 | 7/2015 | Swayze et al. |
| 2015/0203325 A1* | 7/2015 | Briggs ................. B65H 49/36 242/588 |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2018/0360460 A1 | 12/2018 | Mozdzierz et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |

FOREIGN PATENT DOCUMENTS

| | | |
|---|---|---|
| CN | 103156659 A | 6/2013 |
| DE | 1602563 U | 3/1950 |
| DE | 19924311 A1 | 11/2000 |
| DE | 102015221722 A1 | 5/2017 |
| EP | 0327022 A2 | 8/1989 |
| EP | 0594148 A1 | 4/1994 |
| EP | 2491867 A1 | 8/2012 |
| EP | 2762091 A2 | 8/2014 |
| JP | S58175550 A | 10/1983 |
| JP | 2000166933 A | 6/2000 |
| JP | 2001070433 A | 3/2001 |
| JP | 2002202213 A | 7/2002 |
| JP | 2007124166 A | 5/2007 |
| JP | 2010214132 A | 9/2010 |
| JP | H11508791 A | 8/2011 |
| JP | 2013123643 A | 6/2013 |
| JP | 2013154163 A | 8/2013 |
| JP | 2014076351 A | 5/2014 |
| JP | 2014151195 A | 8/2014 |
| JP | 2014171880 A | 9/2014 |
| WO | 9005489 A1 | 5/1990 |

(56) References Cited

FOREIGN PATENT DOCUMENTS

| WO | 9516221 A1 | 6/1995 |
|---|---|---|
| WO | 9838923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report dated Oct. 9, 2019 corresponding to counterpart Patent Application EP 19173353.4.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).

(56) References Cited

OTHER PUBLICATIONS

Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Australian Examination Report No. 1 corresponding to AU 2014200793 dated Sep. 2, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.

(56) References Cited

OTHER PUBLICATIONS

Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686, 105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Office Action corresponding to EP 14 17 2681.0 dated May 13, 2016.
Japanese Office Action for application No. 2019-087596 dated Apr. 4, 2023 with English Translation.
Communication Pursuant to Article 94(3) EPC issued in European Application No. 19 173 353.4 dated Mar. 15, 2023 6 pages.
European Office Action dated May 16, 2023 for European Patent Application No. 19 173 233.8 (8 pages).
Chinese Office Action issued in corresponding Chinese Application No. 201910368757.9 dated Aug. 10, 2023, 20 pages.

\* cited by examiner

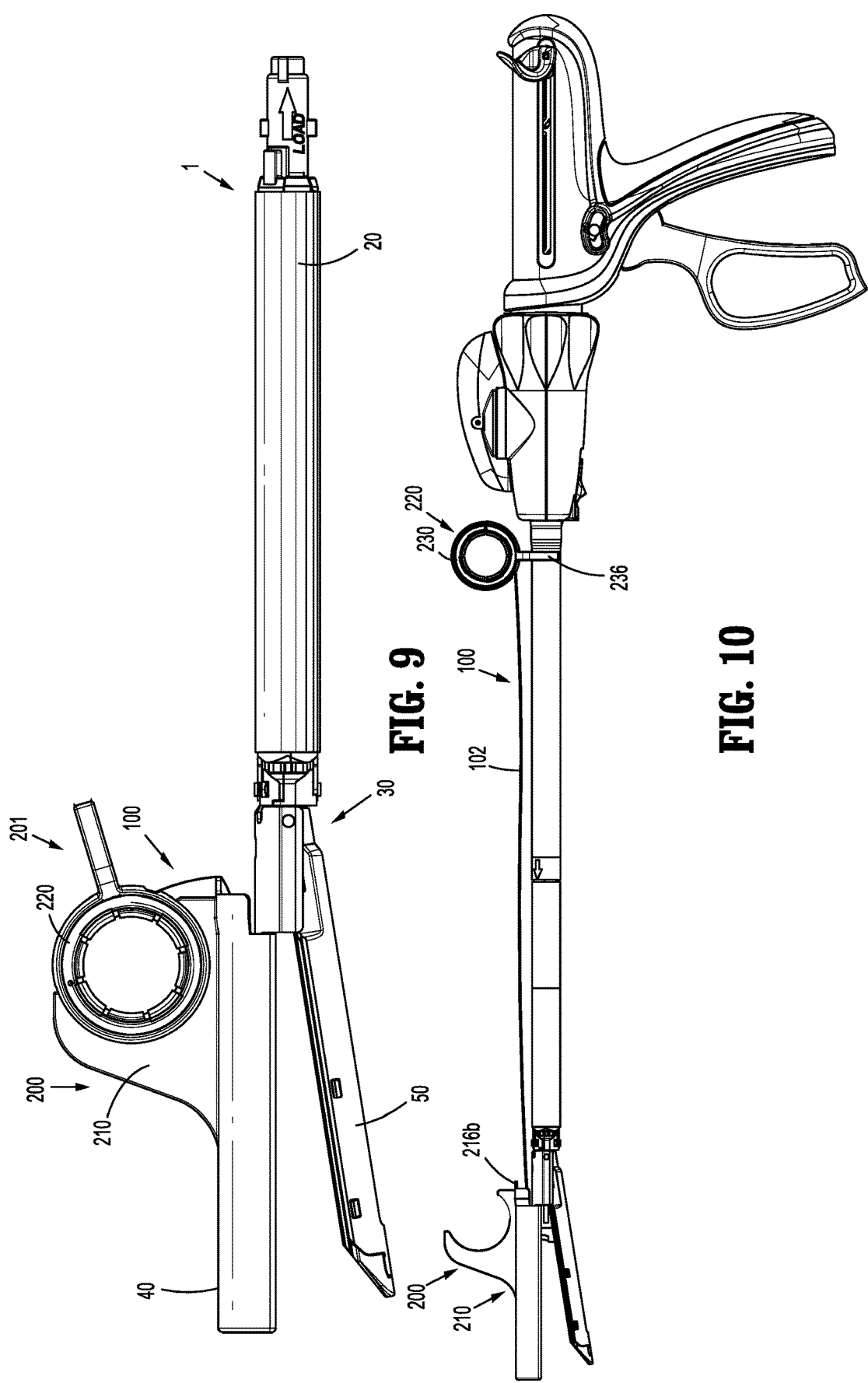

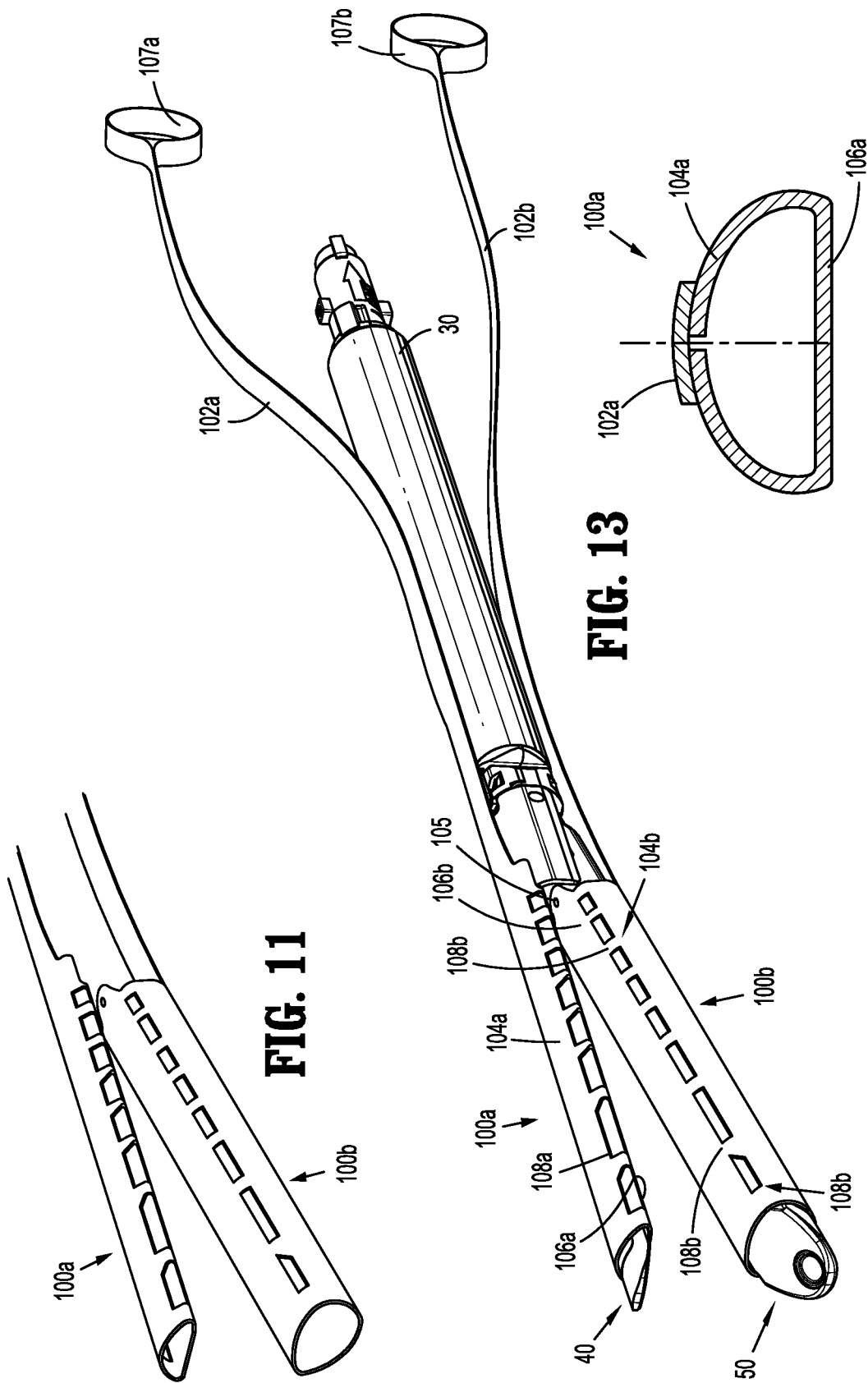

SURGICAL BUTTRESS LOADING AND ATTACHING/DETACHING ASSEMBLIES

CROSS-REFERENCE TO RELATED APPLICATIONS

This application is a continuation of U.S. patent application Ser. No. 16/387,951, filed Apr. 18, 2019 (now U.S. Pat. No. 11,284,896), which claims the benefit of, and priority to, U.S. Provisional Patent Application Ser. No. 62/789,580, filed Jan. 8, 2019, U.S. Provisional Patent Application Ser. No. 62/725,327, filed Aug. 31, 2018, U.S. Provisional Patent Application Ser. No. 62/668,851, filed May 9, 2018, and U.S. Provisional Patent Application Ser. No. 62/668,858, filed May 9, 2018, the entire contents of each of which being hereby incorporated herein by reference.

TECHNICAL FIELD

The present application relates to surgical buttresses for use with surgical stapling apparatus and more particularly, to surgical buttress loading and attaching/detaching assemblies for releasably securing the surgical buttress to a surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together and/or creating anastomoses.

Linear surgical stapling apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in one of the jaws of the apparatus to cut the body tissue between the lines of staples.

Annular surgical stapling apparatus generally include a staple cartridge assembly including annular rows of staples, an anvil assembly operatively associated with the staple cartridge assembly, and an annular blade disposed internal to the annular rows of staples. In use, during an end-to-end circular anastomosis procedure, two ends of hollow tissue sections (e.g., bowels, intestines, or other tubular organs) are positioned between the anvil and staple cartridge assemblies and are joined by clamping the two ends together and driving the annular rows of staples through the clamped tissue sections. During firing of the staples, the annular blade is advanced to cut portions of the tissue sections extending inside the staple lines, thereby establishing a passage through the two stapled tissue sections.

Surgical supports, e.g., meshes or buttress materials, may be used in combination with surgical stapling apparatus to bridge, repair, and/or reinforce tissue defects within a patient such as those occurring, for example, in the abdominal wall, chest wall, diaphragm, or musculo-aponeurotic areas of the body. The buttress material reinforces the staple line as well as covers the juncture of the tissues to reduce leakage prior to healing. The buttress material can help promote proper staple formation while reducing twisting/malformation caused by any misalignment of tissue and/or unusual or non-uniform tissue. The buttress material can also provide support to weakened tissue, or help address differences in the thickness of tissues.

Accordingly, buttress materials provide clinical benefits. Nonetheless, improvements are desired, for example, to reduce the complexity of manufacture and/or application of the buttress materials onto surgical stapling apparatus or into tissue, or to expand the range of application for use of the buttress materials.

SUMMARY

In an aspect of the present disclosure, a surgical buttress loading assembly for use with a surgical stapling apparatus includes a surgical buttress and a surgical buttress applicator. The surgical buttress includes a tubular body and an elongate member extending from the tubular body. The surgical buttress applicator includes a base and a handle releasably engaged with the base. The elongate member is disposed within and extends through the handle, and the tubular body of the surgical buttress is positioned within a cavity of the base.

The base of the surgical buttress applicator may include an elongate body having a proximal end defining an opening into the cavity, and a closed distal end. In embodiments, a tab extends proximally from the proximal end of the elongate body of the base and between the handle and the cavity of the base, and is positioned through an aperture defined in the elongate member of the surgical buttress. In some embodiments, a tab extends proximally from the proximal end of the elongate body of the base, and is positioned through an aperture defined in the tubular body of the surgical buttress.

The base of the surgical buttress applicator may include a fin having a concave wall defining an arcuate cut-out configured to receive the handle therein. The handle of the surgical buttress applicator may include an outer wall defining a groove therein that is configured to receive the concave wall of the base therein to releasably retain the handle within the arcuate cut-out of the base.

The handle of the surgical buttress application may include an outer handle housing including an outer wall and an inner wall defining an annular cavity therebetween. The elongate member of the surgical buttress may be disposed within the annular cavity of the outer handle housing. In embodiments, the outer wall of the outer handle housing includes a slot defined therethrough that is in fluid communication with the annular cavity, and the elongate member of the surgical buttress extends through the slot.

In embodiments, the handle of the surgical buttress application includes an inner handle housing rotatably disposed within the annular cavity of the outer handle housing, and the elongate member of the surgical buttress is wrapped around the inner handle housing. In some embodiments, the inner wall of the outer handle housing includes flexible wall segments extending radially around a central opening defined in the outer handle housing. At least one of the flexible wall segments may include a lip extending therefrom to aid in retaining the inner handle housing within the annular cavity of the outer handle housing. In some embodiments, the inner handle housing includes an annular base including an inner surface configured to engage and be rotatably mounted on the inner wall of the outer handle housing. The inner handle housing may include annular flanges extending from opposed sides of the annular base to aid in retaining the elongate member of the surgical buttress on an outer surface of the annular base.

In another aspect of the present disclosure, a surgical stapling system includes a surgical stapling apparatus and a surgical buttress loading assembly. The surgical stapling apparatus includes a handle assembly, an elongate tubular body portion extending distally from the handle assembly, and an end effector extending distally from the elongate tubular body portion. The end effector includes an anvil assembly and a staple cartridge assembly. The surgical buttress loading assembly includes a surgical buttress and a surgical buttress applicator. The surgical buttress includes a tubular body and an elongate member extending from the tubular body. The surgical buttress applicator includes a base and a handle releasably engaged with the base. The elongate member is disposed within and extends through the handle, and the tubular body of the surgical buttress is positioned within a cavity of the base. The cavity of the base is sized and shaped to slidably receive at least one of the anvil assembly or the staple cartridge assembly of the surgical stapling apparatus therein.

In embodiments, the tubular body of the surgical buttress includes a buttress portion and a folded portion, and the base of the surgical buttress applicator includes a first wall portion configured to extend over a tissue facing surface of the anvil or the staple cartridge assembly and a second wall portion configured to extend around the anvil or the staple cartridge assembly and over an outwardly facing surface of the anvil or staple cartridge assembly. The buttress portion of the surgical buttress is positioned adjacent to the first wall portion and the folded portion is positioned adjacent to the second wall portion such that the tubular body of the surgical buttress is open to receive the anvil or staple cartridge assembly therein.

The handle of the surgical buttress applicator may include a pair of fingers extending from an outer wall thereof that are configured to releasably engage the elongate tubular body portion of the surgical stapling apparatus.

In yet another aspect of the present disclosure, a method of using a surgical buttress loading assembly with a surgical stapling apparatus includes: sliding a surgical buttress loading assembly onto an anvil assembly or a staple cartridge assembly of a surgical stapling apparatus to dispose the anvil or staple cartridge assembly within a tubular body of the surgical buttress, the surgical buttress loading assembly including: a surgical buttress including a tubular body and an elongate member extending from the tubular body; and a surgical buttress applicator including a base and a handle releasably engaged with the base, the elongate member disposed within and extending through the handle, and the tubular body of the surgical buttress positioned within a cavity of the base.

The method may further include detaching the handle of the surgical buttress applicator from the base; and sliding the base of the surgical buttress applicator off of the anvil or staple cartridge assembly, leaving the tubular body of the surgical buttress disposed over the anvil or staple cartridge assembly.

In embodiments, the method further includes attaching the handle of the surgical buttress applicator to the elongate tubular body portion of the surgical stapling apparatus. In some embodiments, the method further includes: firing the surgical stapling apparatus to drive fasteners through a buttress portion of the tubular body of the surgical buttress; and pulling the handle of the surgical buttress applicator away from the buttress portion to separate the elongate member and a folded portion of the tubular body of the surgical buttress from the buttress portion.

In an aspect of the present disclosure, a surgical stapling system includes a surgical stapling apparatus and a staple cartridge surgical buttress assembly. The surgical stapling apparatus includes a handle assembly, an elongate tubular body extending distally from the handle assembly, and an end effector extending distally from the elongate tubular body. The end effector includes an anvil assembly and a staple cartridge assembly. The staple cartridge surgical buttress assembly includes a surgical buttress and a leash. The surgical buttress includes a body having an annular configuration and legs extending from the body. The body is positioned against a tissue facing surface of the staple cartridge assembly and the legs are positioned against a housing of the staple cartridge assembly. The leash is threaded through at least one of the legs and extends proximally from the surgical buttress towards the handle assembly.

Each of the legs of the surgical buttress may include at least one opening or cutout defined therein. The legs of the surgical buttress may alternate between including at least one opening and at least one cutout defined therein. In embodiments, a central portion of the leash is looped through a pair of openings defined in a first leg of the legs of the surgical buttress, and first and second elongated portions of the leash are passed around the housing of the staple cartridge assembly and through an opening defined in a second leg of the legs of the surgical buttress that is opposed to the first leg. In some embodiments, third and fourth legs of the legs of the surgical buttress each include a pair of opposed cutouts defined therein, and the first and second elongated portions of the leash respectively extend under the pair of opposed cutouts.

Free ends of the legs of the surgical buttress may be secured to the housing of the staple cartridge assembly. A sleeve tube may be positioned around the housing of the staple cartridge assembly and over free ends of the legs of the surgical buttress to retain the legs against the staple cartridge assembly.

In embodiments, the surgical stapling system further includes an anvil surgical buttress assembly. The anvil surgical buttress assembly includes a surgical buttress and an anvil cap. The surgical buttress includes a body having an annular configuration and legs extending from the body. The body is positioned against a tissue facing surface of the anvil assembly and the legs are positioned against a distal surface of a housing of the anvil assembly. The anvil cap is coupled to the housing of the anvil assembly. The anvil cap is movable between an approximated position in which the legs of the surgical buttress are captured between the anvil cap and the housing of the anvil assembly and an unapproximated position in which the anvil cap is spaced from the housing and the legs of the surgical buttress are released.

In embodiments, the anvil cap includes a cap body supported on the distal surface of the housing and pegs extending proximally from the cap body. The pegs are positioned through openings defined in the housing. In some embodiments, the pegs of the anvil cap have flanged ends. In certain embodiments, each of the pegs of the anvil cap has a split body including first and second legs terminating at the flanged ends, the first and second legs deflectable inwardly and outwardly relative to each other.

In another aspect of the present disclosure, a staple cartridge assembly includes a housing, a staple guide, a surgical buttress, and a leash. The staple guide is supported within the housing and includes a tissue facing surface having staple receiving slots defined therein. Each of the staple receiving slots houses a staple therein. The surgical buttress includes a body having an annular configuration and legs extending from the body. The body is positioned against the tissue facing surface of the staple guide and the legs are positioned against the housing. The leash is threaded through at least one of the legs and extends proximally from the surgical buttress.

Each of the legs of the surgical buttress may include at least one opening or cutout defined therein. The legs of the surgical buttress may alternate between including at least one opening and at least one cutout defined therein. In embodiments, a central portion of the leash is looped through a pair of openings defined in a first leg of the legs of the surgical buttress, and first and second elongated portions of the leash are passed around the housing and through an opening defined in a second leg of the legs of the surgical buttress that is opposed to the first leg. In some embodiments, third and fourth legs of the legs of the surgical buttress each include a pair of opposed cutouts defined therein, and the first and second elongated portions of the leash respectively extend under the pair of opposed cutouts.

Free ends of the legs of the surgical buttress may be secured to the housing. A sleeve tube may be positioned around the housing and over free ends of the legs of the surgical buttress to retain the legs against the housing.

BRIEF DESCRIPTION OF THE DRAWINGS

The above and other aspects, features, and advantages of the present disclosure will be apparent in light of the following detailed description when taken in conjunction with the accompanying drawings, which are incorporated in and constitute a part of this specification, wherein:

FIG. 9 is a side view of the surgical stapling apparatus of FIG. 1 including the surgical buttress loading assembly of FIG. 6 disposed thereon;

FIG. 10 is a side view of a surgical stapling apparatus including the surgical buttress loading assembly of FIG. 9, illustrating a handle of the surgical buttress applicator separated from a base of the surgical buttress applicator;

FIG. 11 is a perspective view of anvil and cartridge buttresses in accordance with another embodiment of the present disclosure;

FIG. 12 is a cross-sectional view of the anvil buttress of FIG. 11;

FIG. 13 is a perspective view of an end effector having the anvil and cartridge buttresses of FIG. 11 disposed thereon in accordance with an embodiment of the present disclosure

DETAILED DESCRIPTION OF EMBODIMENTS

Figure 1:
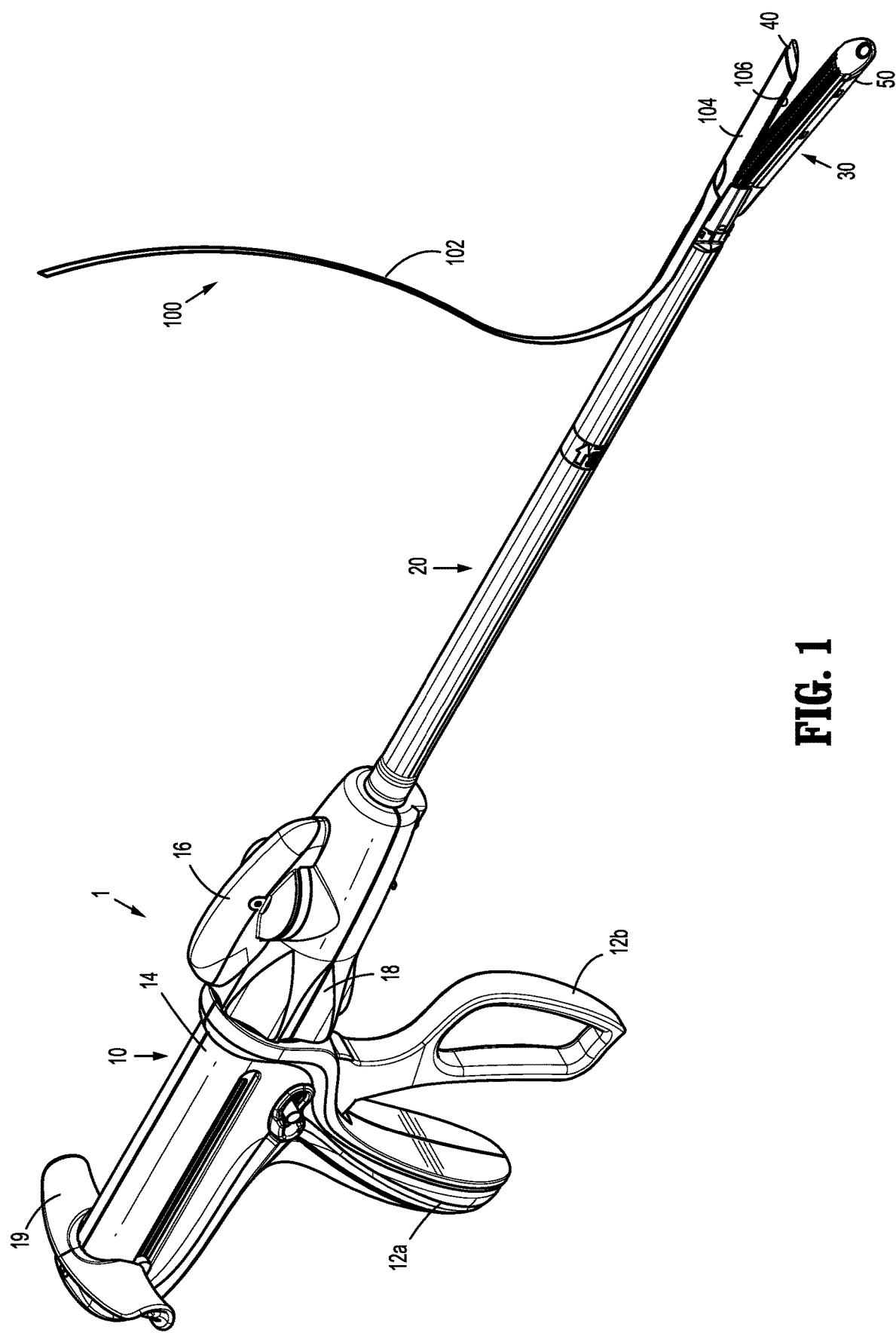
FIG. 1 is a perspective view of a surgical stapling apparatus having a surgical buttress disposed thereon in accordance with an embodiment of the present disclosure.

Embodiments of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are used to ease description of the embodiments and are not intended to have any limiting effect on the ultimate orientation of a structure or any part thereof. In the following description, well-known functions or constructions are not described in detail to avoid obscuring the present disclosure in unnecessary detail.

Referring now to FIG. 1, an exemplary surgical stapling apparatus or surgical stapler 1 in the form of a linear surgical stapling device is shown for use in stapling tissue and applying one or more buttress materials or surgical buttresses to the tissue. The surgical stapling apparatus 1 generally includes a handle assembly 10, an elongate tubular body portion 20 extending distally from the handle assembly 10, and an end effector or jaw assembly 30 extending distally from the elongate tubular body portion 20. The jaw assembly 30 includes an anvil assembly 40 and a staple cartridge assembly 50. The jaw assembly 30 may be permanently affixed to the elongate tubular body portion 20 or may be detachable with respect to the elongate tubular body portion 20 and thus, replaceable with a new jaw assembly 30. The anvil assembly 40 and/or the staple cartridge assembly 50 is pivotable with respect to the elongate tubular body portion 20 such that the anvil and/or staple cartridge assemblies 40, 50 is movable between an open position in which the anvil and staple cartridge assemblies 40, 50 are spaced apart with respect to each other and a closed position in which the anvil and staple cartridge assemblies 40, 50 are substantially adjacent each other.

The handle assembly 10 includes a stationary handle member 12a, a movable handle member 12b, and a barrel portion 14. An articulation lever 16 is mounted on the forward end of the barrel portion 14 to facilitate articulation of the jaw assembly 30. A rotatable member 18 is also mounted on the forward end of the barrel portion 14, adjacent the articulation lever 16. Rotation of the rotatable member 18 relative to the barrel portion 14 rotates the elongate tubular body portion 20 and the jaw assembly 30 relative to the handle assembly 10 so as to properly orient the anvil and staple cartridge assemblies 40, 50 relative to tissue to be stapled. A knob 19 is movably positionable along the barrel portion 14. The knob 19 is advanced distally to approximate or close the anvil and staple cartridge assemblies 40, 50, relative to each other, and retracted proximally to unapproximate or open the anvil and staple cartridge assemblies 40, 50, with respect to each other. Actuation of the movable handle member 12b applies lines of staples 58 (FIG. 2) to tissue captured between the anvil and staple cartridge assemblies 40, 50.

Figure 2:
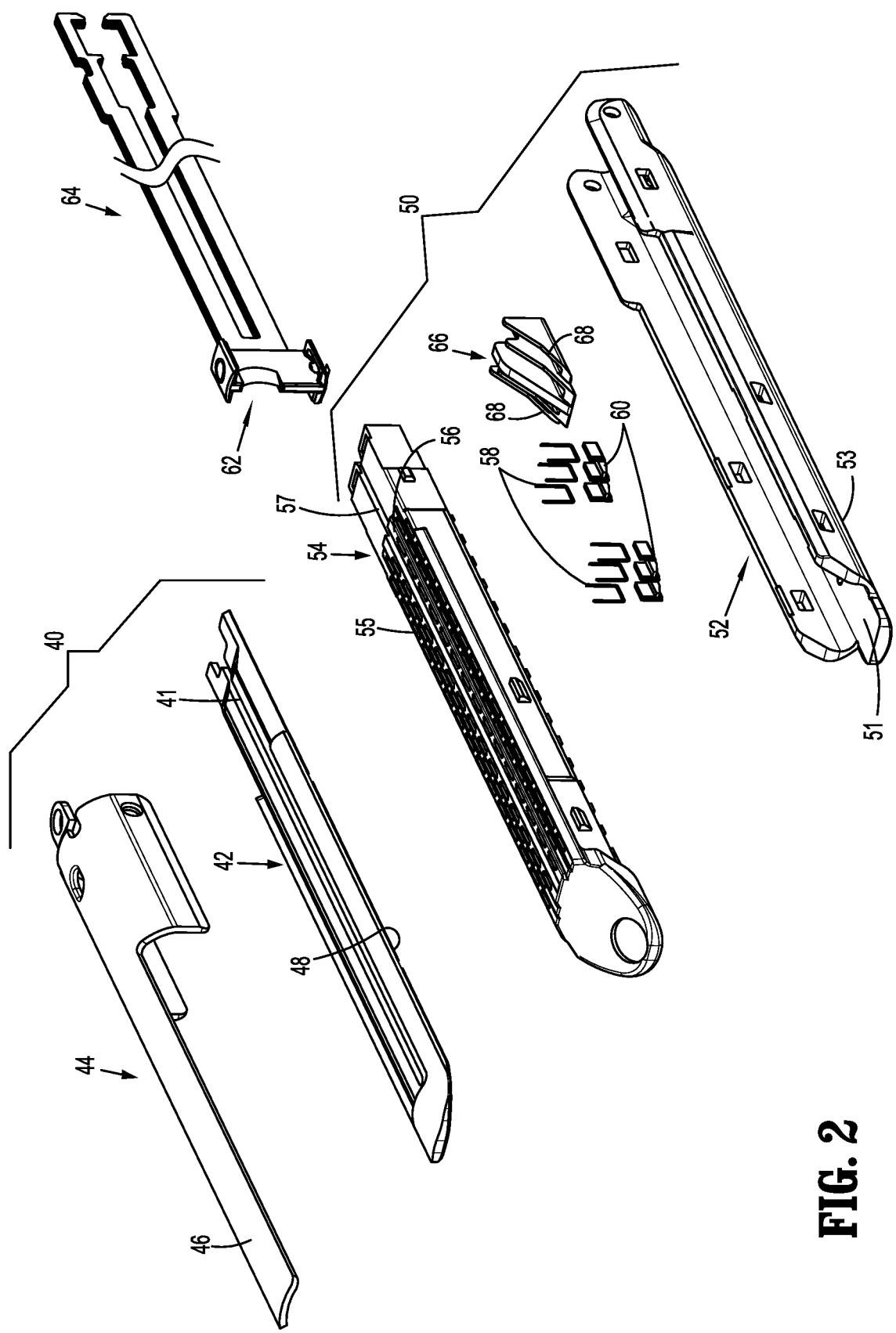
FIG. 2 is an exploded, perspective view of anvil and staple cartridge assemblies of an end effector of the surgical stapling apparatus of FIG. 1.

As shown in FIG. 2, the anvil assembly 40 includes an anvil plate 42 having a central longitudinal slot 41 formed therein, and a cover plate 44 secured over the anvil plate 42 such that the cover plate 44 defines a top or outwardly facing surface 46 of the anvil assembly 40. The anvil plate 42 may include a plurality of staple forming pockets/cavities (not shown) defined in an inwardly or tissue facing surface 48 thereof.

The staple cartridge assembly 50 includes a cartridge carrier 52 defining an elongated support channel 51 configured and dimensioned to selectively receive a staple cartridge 54 therein. The cartridge carrier 52 also defines a bottom or outwardly facing surface 53 of the staple cartridge assembly 50. The staple cartridge 54 is removable and replaceable in the cartridge carrier 52 of the staple cartridge assembly 50. The staple cartridge 54 includes an inwardly or tissue facing surface 56 defining staple pockets or retention slots 55 formed therein for receiving a plurality of fasteners or staples 58 and staple pushers 60. A central longitudinal slot 57 is formed in and extends along a substantial length of the staple cartridge 54 to facilitate passage of a knife blade 62 of a drive bar 64 therethrough. During operation of the surgical stapler 1, an actuation sled 66 translates through the staple cartridge 54 to advance cam wedges 68 of the actuation sled 66 into sequential contact with the staple pushers 60, to cause the staple pushers 60 to translate vertically within the staple pockets 55 and urge the staples 58 from the staple pockets 55 towards the tissue facing surface 48 of the anvil plate 42 of the anvil assembly 40.

For a detailed description of the structure and function of exemplary surgical stapling apparatus, reference may be made to U.S. Pat. Nos. 8,256,656, 7,819,896, and 7,128,253, the entire content of each of which is incorporated herein by reference. It should be appreciated that principles of the present disclosure are equally applicable to surgical stapling apparatus having other configurations such as, for example, the types described in U.S. Pat. Nos. 7,334,717, 5,964,394, and 5,915,616, the entire content of each of which is incorporated herein by reference. Accordingly, it should be understood that a variety of surgical stapling apparatus may be utilized with the surgical buttresses and/or surgical buttress applicators of the present disclosure such as, for example, laparoscopic staplers, open staplers, transverse anastomosis staplers, and end-to-end anastomosis staplers having a circular staple cartridge and anvil, as well as staple cartridge assemblies housing surgical fasteners other than staples.

With reference again to FIG. 1, a surgical buttress 100 is shown releasably coupled to the anvil assembly 40 of the surgical stapler 1. The surgical buttress 100 is fabricated from biocompatible materials which are bioabsorbable or non-absorbable, natural or synthetic materials. It should be understood that any combination of natural, synthetic, bioabsorbable, and/or non-bioabsorbable materials may be used to form the surgical buttress 100. The surgical buttress 100 may be biodegradable (e.g., formed from bioabsorbable and bioresorable materials) such that the surgical buttress 100 decomposes or is broken down (physically or chemically) under physiological conditions in the body, and the degradation products are excretable or absorbable by the body. Components or portions of the surgical buttress 100 may be formed from the same material or different materials.

In embodiments, at least a portion of the surgical buttress 100 is made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, at least a portion of the surgical buttress 100 is made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes.

The surgical buttress 100 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttress 100, or portions thereof, may be a non-woven structure formed by melt-blown or melt-spun methods, a mesh material, a braid material, and/or a molded or extruded sheet. The surgical buttress 100, or portions thereof, may be a single porous or non-porous layer, or include a plurality of layers including any combination of porous and/or non-porous layers.

Figure 3:
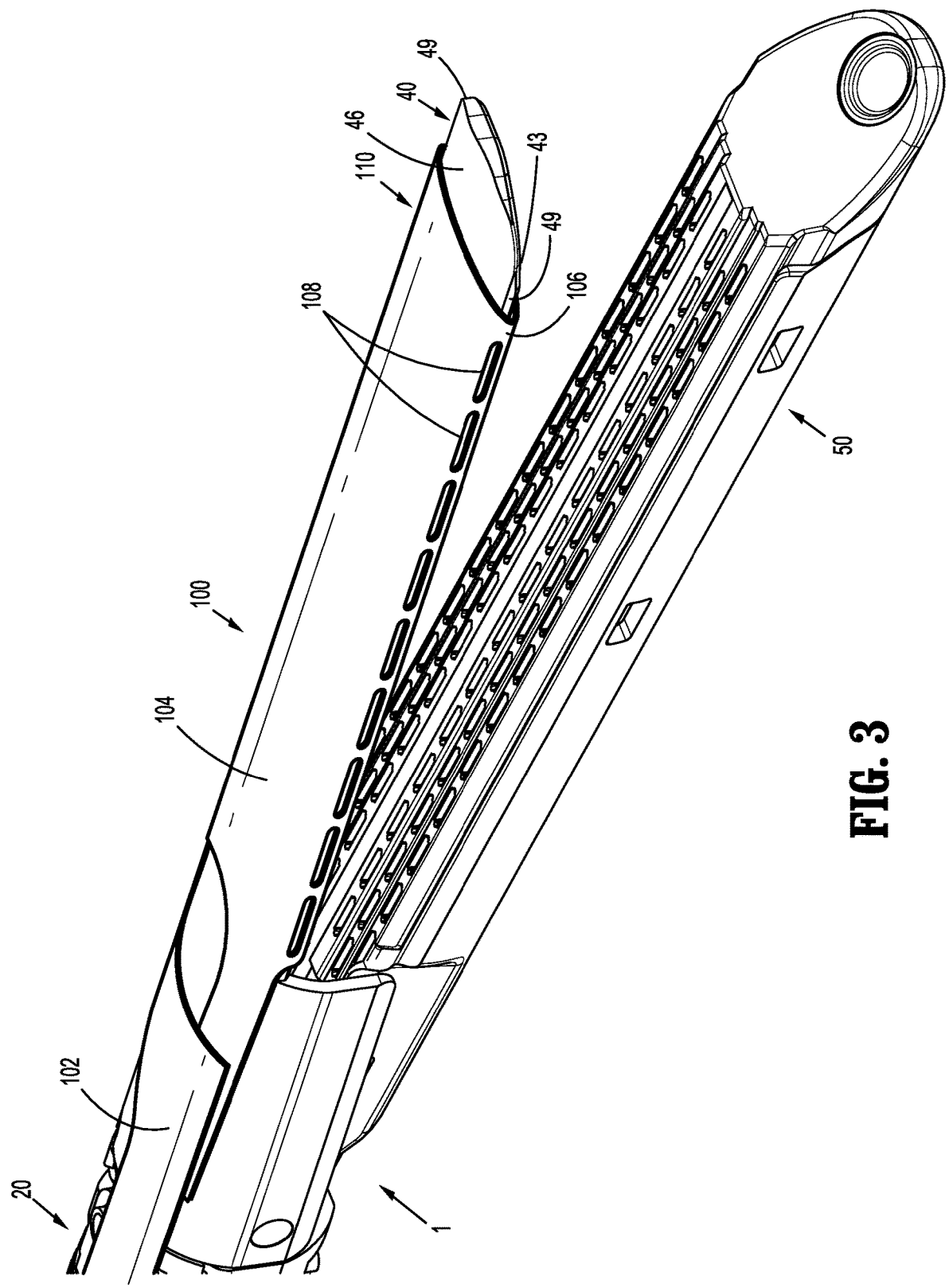
FIG. 3 is a perspective view of an end effector of the surgical stapling apparatus of FIG. 1, showing the surgical buttress disposed thereon.
Figure 4:
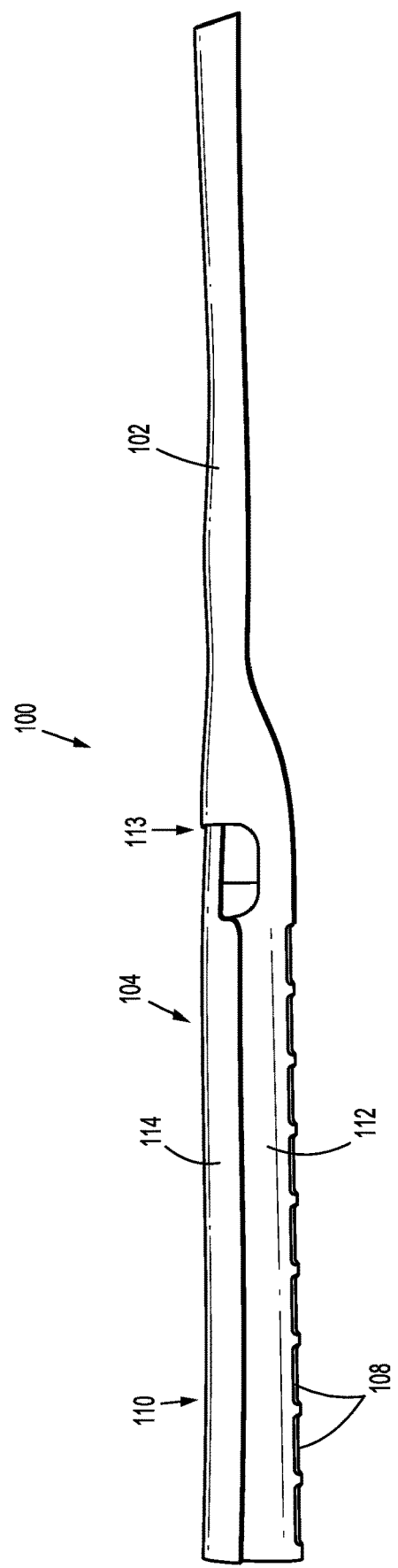
FIG. 4 is a side view of the surgical buttress of FIG. 1, separated from the surgical stapling apparatus.

As shown in FIGS. 3 and 4, the surgical buttress 100 includes an elongate member 102, a folded portion 104, and a buttress portion 106. The elongate member 102 is coupled to the folded portion 104, and the folded portion 104 is coupled to the buttress portion 106 and is separable therefrom by perforations 108. Together, the folded portion 104 and the buttress portion 106 form a tubular body 110 that is sized and shaped to facilitate the reception of the anvil assembly 40 and/or the staple cartridge assembly 50 therethrough.

The elongate member 102 is secured to the folded portion 104 of the surgical buttress 100 and extends proximally therefrom. The elongate member 102 is of a sufficient length to be accessible outside of a patient's body and may extend the length of the elongate tubular body portion 20 of the surgical stapler 1. The elongate member 102 may be a band, a cord, a rope, a strap, a suture, among other elongate structures tethered to or integrally formed with the folded portion 104 of the surgical buttress 100. In some embodiments, the elongate member 102 may include two or more elongate sections such as, for example, a suture attached to a strip of material that extends proximally from the folded portion 104 of the surgical buttress 100.

When the elongate member 102 is pulled away from the tubular body 110 (e.g., proximally towards a user), the folded portion 104 and the elongate member 102 separate from the buttress portion 106 along the perforations 108. It should be understood, however, that the perforations 108 may be omitted from the surgical buttress 100. For example, the juncture between the folded portion 104 and the buttress portion 106 may be formed or otherwise secured to one another to facilitate separation of the folded portion 104 from the buttress portion 106 upon application of a force to the elongate member 102.

The folded portion 104 can include one or more sections of material, and can be made from the same material as the buttress portion 106, or from a different material, as discussed above. The folded portion 104 can be secured to itself to form the tubular body 110 and/or the buttress portion 106 can be attached to the folded portion 104 or itself. The folded portion 104 and/or the buttress portion 106, or sections thereof, may be integrally formed or secured together via any suitable attachment features within the purview of those skilled in the art, such as, mechanical attachment features (e.g., sutures, pins), chemical attachment features (e.g., adhesives), and/or attachment methods (e.g., welding).

The folded portion 104 can include first and second sections 112, 114 secured to one another. In embodiments, the first and second sections 112, 114 are welded to each other. The elongate member 102 can be unitary with the folded portion 104 and/or may be permanently secured to the folded portion 104. As seen in FIG. 4, the elongate member 102 can be integrally formed with the first section 112 of the folded portion 104 and attached to the second section 114 by welding at an attachment region 113. The elongate member 102 can include one or more elongate sections, as discussed above, and can be made from the same material, or different material, as the folded and/or buttress portions 104, 106.

With continued reference to FIG. 3, the surgical buttress 100 is disposed on the anvil assembly 40 of the stapler 1 with the buttress portion 106 positioned over the tissue facing surface 48 of the anvil assembly 40, the folded portion 104 positioned over the outwardly facing surface 46 of the anvil assembly 40, and the elongate member 102 extending proximally along the elongate tubular body portion 20 of the surgical stapler 1. The perforations 108 are positioned adjacent side surfaces 49 of the anvil assembly 40 that interconnect the outwardly and tissue facing surfaces 46, 48 of the anvil assembly 40.

The perforations 108 can be any size and shape, such as small pin-holes or larger openings such as, for example, the elongated openings shown in FIG. 3, or the perforations 108 can be a single feature, such as a line of weakness in the buttress material or materials forming the folded and buttress portions 104, 106. The perforations 108 may be formed using laser cutting, knife cutting, press cutting, scoring, etching, among other methods within the purview of those skilled in the art. In some embodiments, the surgical buttress 100 is formed from a non-woven polyglycolide material that is laser cut to form the perforations 108.

Figure 5:
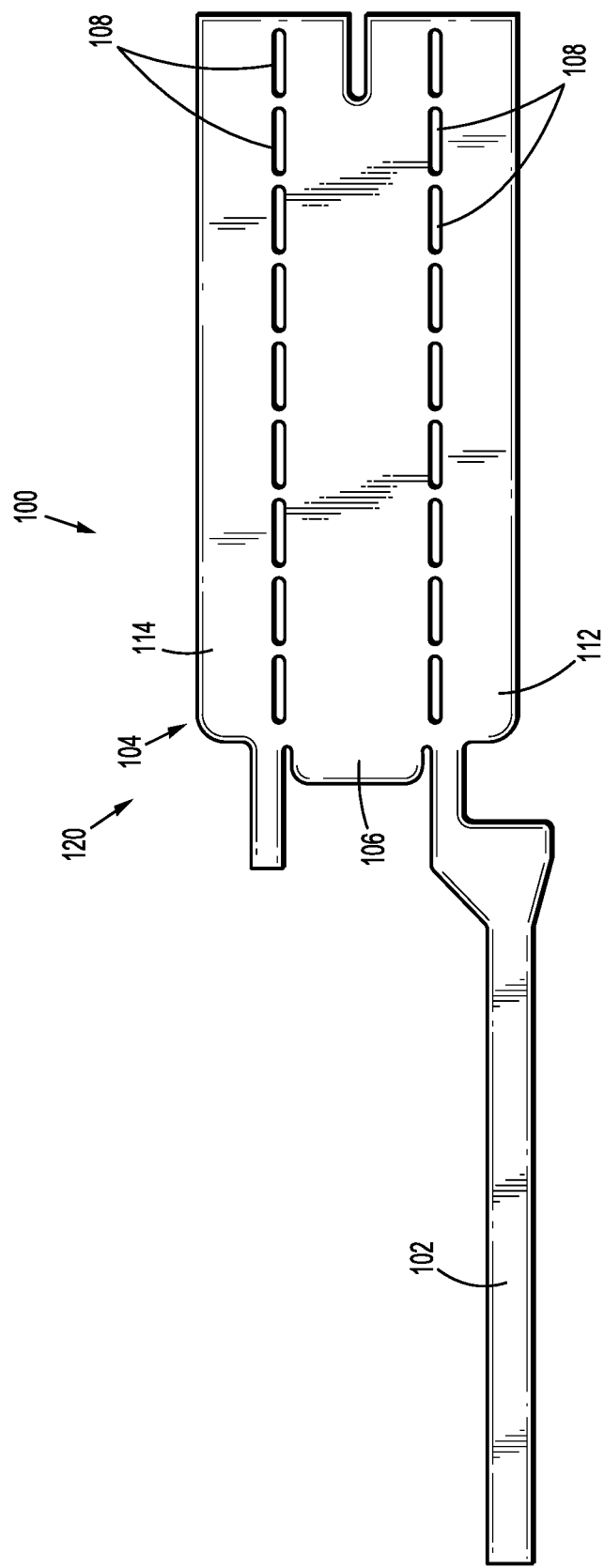
FIG. 5 is a plan view of the surgical buttress of FIG. 4, in an unfolded condition in accordance with an embodiment of the present disclosure.

As shown in FIG. 5, the entire surgical buttress 100 may be formed from a single sheet of material 120. The surgical buttress 100 is cut from the single sheet of material 120 and the perforations 108 are formed therein. The single sheet of material 120 is cut such that the surgical buttress 100 includes the elongate member 102, the folded portion 104 including first and second sections 112, 114, and the buttress portion 106. The first and second sections 112, 114 of the folded portion 104 can be folded and attached to one another before the surgical buttress 100 is disposed on or around the anvil assembly 40 of the surgical stapler 1 (e.g., prior to loading the surgical buttress 100 into a surgical buttress applicator 200 (FIG. 6)), or as the surgical buttress 100 is applied to the anvil assembly 40. As discussed above, the first and second sections 112, 114 of the folded portion 104 can be attached to one other by, for example, welding, using adhesives, tying sutures, etc.

Figure 6:
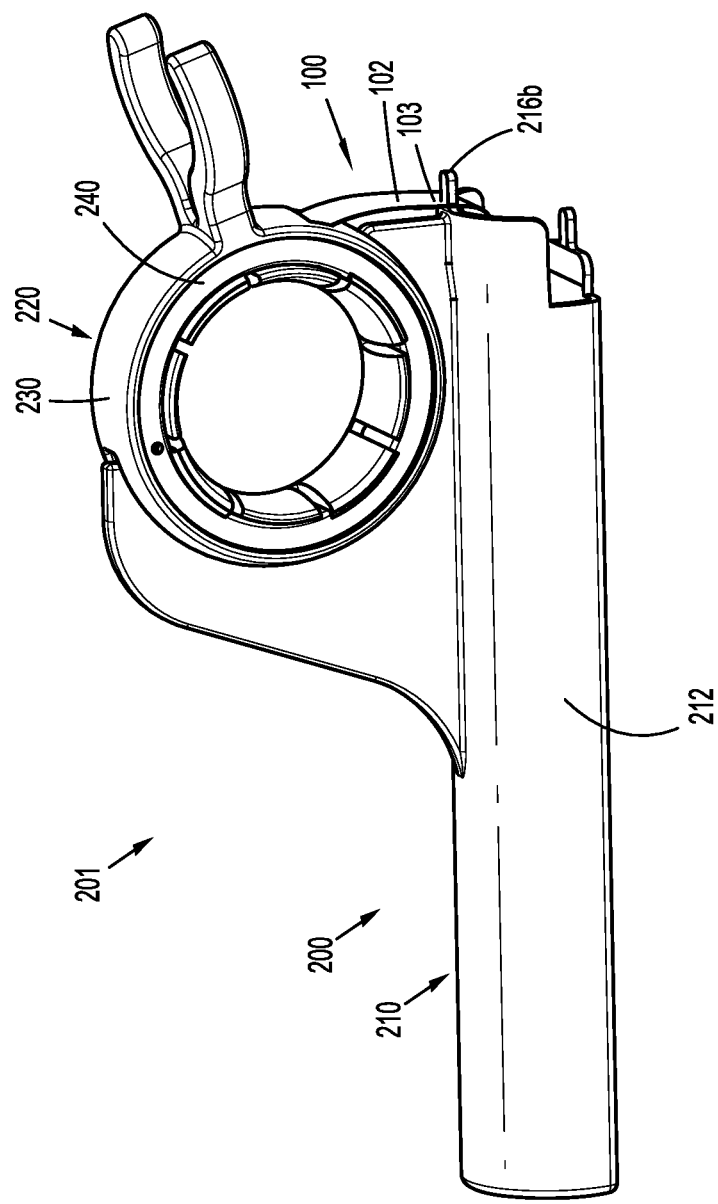
FIG. 6 is a side, perspective view of a surgical buttress loading assembly including a surgical buttress applicator and a surgical buttress in a loaded configuration in accordance with an embodiment of the present disclosure.

Turning now to FIG. 6, a surgical buttress loading assembly 201 is shown. The surgical buttress loading assembly 201 includes a surgical buttress applicator 200 configured for positioning the surgical buttress 100 onto a surgical stapler 1 (FIG. 1) and/or removing the elongate member 102 and the folded portion 104 (FIG. 1) of the surgical buttress 100 from a surgical site. The surgical buttress applicator 200 includes a base 210 sized and shaped to releasably retain the tubular body 110 (FIG. 3) of the surgical buttress 100 therein, and a handle 220 configured to retain the elongate member 102 of the surgical buttress 100 therein.

Figure 7:
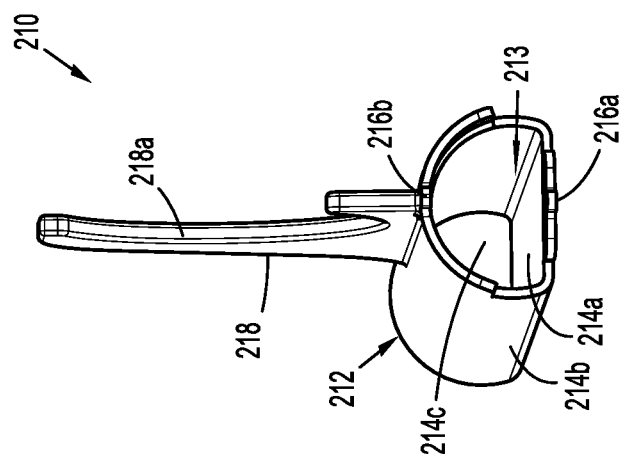
FIG. 7 is an end, perspective view of a base of the surgical buttress applicator of FIG. 6.
Figure 8:
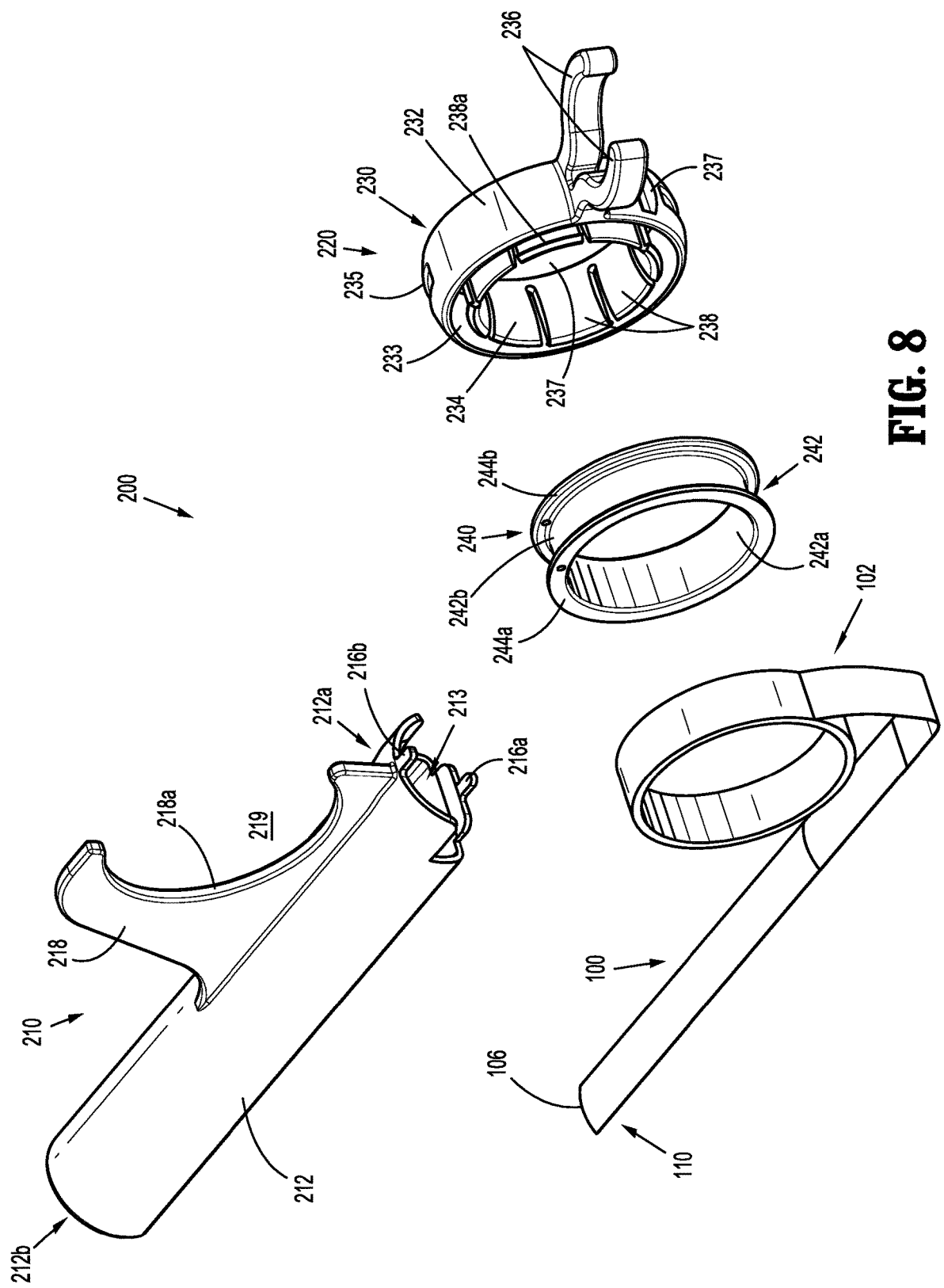
FIG. 8 is a perspective view, with parts separated, of the surgical buttress loading assembly of FIG. 6.

As shown in FIGS. 7 and 8, the base 210 includes an elongate body 212 having a proximal end 212a and a distal end 212b, and defines a cavity 213 therein. The cavity 213 is sized and shaped to slidably receive at least one of the anvil or staple cartridge assembly 40, 50 (FIG. 1) of the surgical stapler 1 therein. The elongate body 212 includes a first or substantially flat wall section 214a corresponding to the tissue facing surface 48, 56 (FIG. 2) of the anvil or staple cartridge assembly 40, 50 of the surgical stapler 1, and a second or rounded wall section 214b configured to extend around the anvil or staple cartridge assembly 40, 50 and over the outwardly facing surface 46, 53 (FIG. 2) of the anvil or staple cartridge assembly 40, 50.

The proximal end 212a of the elongate body 212 defines an opening into the cavity 213 of the base 210, and the distal end 212b is closed by a distal wall section 214c. It is envisioned, however, that the distal end 212b of the elongate body 212 may be open. The proximal end 212a further includes first and second tabs 216a, 216b extending proximally and axially from the respective first and second wall sections 214a, 214b of the elongate body 212 in opposed relation relative to each other. The first and second tabs 216a, 216b are configured to engage the surgical buttress 100.

The base 210 of the surgical buttress applicator 200 further includes a fin 218. The fin 218 extends from the second wall section 214b of the elongate body 212. The fin 218 includes a concave wall 218a defining an arcuate cut-out 219 configured to receive the handle 220 therein.

With reference now to FIGS. 6 and 8, the handle 220 includes an outer handle housing 230 and an inner handle housing 240 rotatably disposed within the outer handle housing 230. The elongate member 102 of the surgical buttress 100 is spooled, wound or rolled around the inner handle housing 240 and extends through a slot 237 defined through the outer handle housing 230 such that the tubular body 110 of the surgical buttress 100 is positionable within the cavity 213 of the base 210.

The outer handle housing 230 includes an outer wall 232 and an inner wall 234 defining an annular cavity 233 therebetween. The outer wall 232 includes a groove 235 defined therein that corresponds with, and is configured to frictionally engage, the concave wall 218a of the fin 218 of the base 210 to releasably retain the handle 220 within the arcuate cut-out 219 of the base 210. The outer handle housing 230 further includes a pair of fingers 236 extending from the outer wall 232 that are configured to releasably engage the elongate tubular body portion 20 (FIG. 1) of the surgical stapler 1, and a slot 237 defined through the outer wall 232 that is sized and shaped for passage of the elongate member 102 of the surgical buttress 100 therethrough.

The inner wall 234 of the outer handle housing 230 includes flexible wall segments 238 extending radially around a central opening 239 defined in the outer handle housing 230. The flexible wall segments 238 are movable to allow a user to insert or remove the inner handle housing 240 into or out of the annular cavity 233 of the outer housing 230. At least one of the flexible wall segments 238 includes a lip 238a extending towards the outer wall 232 to help retain the inner handle housing 240 within the annular cavity 233. In embodiments, at least two flexible wall segments 238 (e.g., opposed flexible wall segments 238) may each include a lip 238a extending therefrom and, in some embodiments, alternating flexible wall segments 238 may each include a lip 238a extending therefrom.

The inner handle housing 240 is concentric with and configured to be received within the annular cavity 233 of the outer handle housing 230. The inner handle housing 240 includes an annular base 242 having an inner surface 242a configured to engage the inner wall 234 of the outer handle housing 230 and to be rotatably mounted thereon. The arcuate base 242 also includes an outer surface 242b that is configured to receive the elongate member 102 of the surgical buttress 100 therearound. Annular flanges 244a, 244b extend from opposed sides of the annular base 242 adjacent respective sides of the elongate member 102 when the elongate member 102 is wrapped around the annular base 242.

In a method of assembling the handle 220, the elongate member 102 of the surgical buttress 100 is wrapped around the outer surface 242b of the annular base 242 of the inner handle housing 240 such that the elongate member 102 conforms to the contour of the annular base 242. The elongate member 102 is wound around the annular base 242 such that a majority of the elongate member 102 is wound around the inner handle housing 240, and the tubular body 110 of the surgical buttress 100 freely extends therefrom. In embodiments, a terminal end of the elongate member 102 may be secured to the inner handle housing 240 and/or to itself (e.g., the terminal end may form a closed loop 107a (FIG. 13) around the inner handle housing) to secure the elongate member 102 to the inner handle housing 240. The tubular body 110 is passed through the slot 237 of the outer handle housing 230 and pulled therethrough, and the inner handle housing 240 is inserted into the annular cavity 233 of the outer handle housing 230.

In a method of assembling the surgical buttress loading assembly 201, the assembled handle 220 is positioned within the arcuate cut-out 219 of the base 210 of the surgical buttress applicator 200, and the tubular body 110 of the surgical buttress 100, which includes the folded and buttress portions 104, 106 of the surgical buttress 100, is positioned within the cavity 213 of the base 210 of the surgical buttress applicator 200. The folded portion 104 of the surgical buttress 100 is positioned adjacent to the second wall section 214b of the base 210 and the buttress portion 106 is disposed adjacent to the first wall section 214a of the base 210 such that the tubular body 110 is open to receive the anvil or staple cartridge assembly 40, 50 therein.

The inner handle member 240 may then be rotated relative to the outer handle member 230 to wind or unwind the elongate member 102 around the inner handle member 240 so that the elongate member 102 is made taut as shown in FIG. 6. In the loaded configuration shown in FIG. 6, the portion of the elongate member 102 extending between the base 210 and the handle 220 of the surgical buttress applicator 200 is secured to the second tab 216b of the base 210 to help retain the tubular body 110 of the surgical buttress 100 within the base 210. The second tab 216b is positioned through an aperture 103 defined through the elongate member 102. The aperture 103 may be formed during assembly of the surgical buttress 100 into the surgical buttress applicator 200, or the aperture 103 may be pre-formed in the surgical buttress 100 prior to assembly. In some embodiments, the first tab 216a of the base 210 of the surgical buttress applicator 200 may be engaged with an aperture 105 (FIG. 13) defined in the buttress portion 106 of the surgical buttress 100 to further help retain the tubular body 110 within the base 210 in an open configuration for receiving the anvil or staple cartridge assembly 40, 50 therein.

In a method of loading the surgical buttress 100 onto the surgical stapler 1, as shown in FIG. 9, the surgical buttress loading assembly 201 is applied to the anvil assembly 40 of the surgical stapler 1. A user grasps the handle 220 of the surgical buttress applicator 200 and manipulates the surgical buttress loading assembly 201 onto the anvil assembly 40 by aligning the cavity 213 (FIG. 7) of the base 210 with the distal end of the anvil assembly 40 and sliding the surgical buttress applicator 200 proximally over the anvil assembly 40 until the anvil assembly 40 abuts the distal wall section 214c (FIG. 7) of the base 210. As discussed above, the shape (e.g., a transverse cross-sectional shape/profile) of the cavity 213 of the base 210 corresponds to the shape (e.g., a transverse cross-sectional shape/profile) of the anvil assembly 40 (or the staple cartridge assembly 50) for ease of application of the surgical buttress 100 thereon.

With the surgical buttress loading assembly 201 applied onto the anvil assembly 40 such that the anvil assembly 40 is received within the tubular body 110 of the surgical buttress 100 as well as within the base 210 of the surgical buttress applicator 200, the handle 220 of the surgical buttress applicator 200 is detached from the base 210 and pulled proximally towards the user, thereby unrolling the elongate member 102 from within the handle 220 of the surgical buttress applicator 200, as shown in FIG. 10. The handle 220 is secured to the elongate tubular body portion 20 of the surgical stapler 1 via the pair of fingers 236 of the outer handle housing 230 at a position proximal of the end effector 30, such as adjacent to the handle assembly 10 (FIG. 1) of the surgical stapler 1, and/or at least at a location outside of a patient's body during a surgical procedure. The user can then grasp the base 210 of the surgical buttress applicator 200 and slide it distally off of the anvil assembly 40. The base 210 may be removed from the anvil assembly 40 either prior to, or after, attaching the handle 220 to the surgical stapler 1. As the base 210 is slid distally, the surgical buttress 100 disengages from the second tab 216b of the base 210 such that the surgical buttress 100 is left loaded on the anvil assembly 40. The surgical stapler 1 is now ready for use.

In a method of use, the loaded surgical stapler 1 is introduced to a surgical site through a trocar or other access device. The surgical stapler 1 is operated within methods known by those skilled in the art. Once the anvil and staple cartridge assemblies 40, 50 are clamped onto tissue, the surgical stapler 1 is fired. In firing the surgical stapler 1, the drive bar 64 (FIG. 2) is advanced distally through the jaw assembly 30 urging the staple pushers 60 upwardly which, in turn, drive the staples 58 out of the staple pockets 55 and through the buttress portion 106 of the surgical buttress 100 as well as the captured tissue, thereby stapling the buttress portion 106 to the tissue. During firing, the knife blade 62 of the drive bar 64 travels distally while substantially simultaneously cutting and dividing the tissue as well as the buttress portion 106 of the surgical buttress 100 disposed between the rows of now formed staples 58.

The folded portion 104 and the elongate member 102 of the surgical buttress 100 can then be detached from the now-stapled buttress portion 106 by pulling the handle 220 proximally to tear the folded portion 104 from the buttress portion 106 via the perforations 108. The handle 220 may be pulled separately from the surgical stapler 1 by detaching the handle 220 from the elongate tubular body portion 20 of the surgical stapler 1, or the handle 220 may be pulled when the surgical stapler 1 is pulled proximally away from the surgical site. Alternatively, the user may grasp an exposed portion of the elongate member 102 and pull the elongate member 102 directly.

It should be understood that additionally or alternatively, a surgical buttress loading assembly may be applied to the staple cartridge assembly of the surgical stapler and/or either the anvil assembly or the staple cartridge assembly can include a buttress material pre-loaded thereon. For example, in surgical stapling apparatus having staple cartridge assemblies that are removable and replaceable, the staple cartridge assembly may have a buttress pre-loaded onto it by the manufacturer. In these circumstances, the user can utilize a surgical buttress loading assembly that is ready for installation on the anvil assembly, as discussed above. In embodiments, the surgical stapling apparatus can be re-used on the same patient by reloading it with a staple cartridge assembly having a fresh set of staples ready to be fired and a fresh buttress material. A new surgical buttress loading assembly may be applied to the anvil assembly, as discussed above, or a fresh surgical buttress may be installed into the surgical buttress applicator, as also discussed above.

Further, the surgical buttress loading assembly can be sized and shaped to correspond to a particular jaw onto which it is to be assembled. For example, a first surgical buttress loading assembly may have a shape corresponding to the shape of the anvil assembly and a second surgical buttress loading assembly may have a shape corresponding to the staple cartridge assembly. As shown in FIG. 1, the anvil assembly 40 has a lower profile and is more curved in shape than the staple cartridge assembly 50, which is deeper and may be rounded or more rectangular in shape. Accordingly, the surgical buttress and the surgical buttress applicator of the present disclosure may be any size and/or shape to accommodate a variety of surgical stapler sizes and/or configurations.

As shown, for example, in FIGS. 11-13, surgical buttresses, shown as anvil and cartridge buttresses 100a, 100b, are respectively configured for use with the anvil and staple cartridge assemblies 40, 50 of the end effector 30 of the surgical stapler 1 (FIG. 1) and likewise, surgical buttress applicators (not shown) are configured for use with the anvil and cartridge buttresses 100a, 100b. The anvil and cartridge buttresses 100a, 100b each include an elongate member 102a, 102b, a folded portion 104a, 104b, and a buttress portion 106a, 106b. Perforations 108a, 108b are disposed between the folded portion 104a, 104b and the buttress portion 106a, 106b of the respective anvil and cartridge buttress 100a, 100b, and are optimized to allow for sequential detachment of the folded portion 104a, 104b from the buttress portion 106a, 106b when the elongate member 102a, 102b is pulled. The folded portion 106a, 106b and the buttress portion 106a, 106b are formed from a single sheet of material having the perforations 108a, 108b formed therein, and the elongate member 102a, 102b is attached to the respective folded portion 106a, 106b. Loops 107a, 107b are disposed at terminal ends of the respective elongate member 102a, 102b and are configured for positioning around the inner handle housing of the respective surgical buttress applicator with which the anvil and cartridge buttresses 100a, 100b are utilized.

The surgical buttress may be provided and/or sold as part of the surgical buttress loading assembly that includes the surgical buttress and the surgical buttress applicator. Alternatively, the surgical buttress and the surgical buttress applicator may be provided and/or sold separately and assembled by the user. In embodiments, one or more surgical buttresses and one or more surgical buttress applicators are provided in a kit. In some embodiments, the kit further includes one or more end effectors and, in certain embodiments, the kit further includes a surgical stapler.

Figure 14:
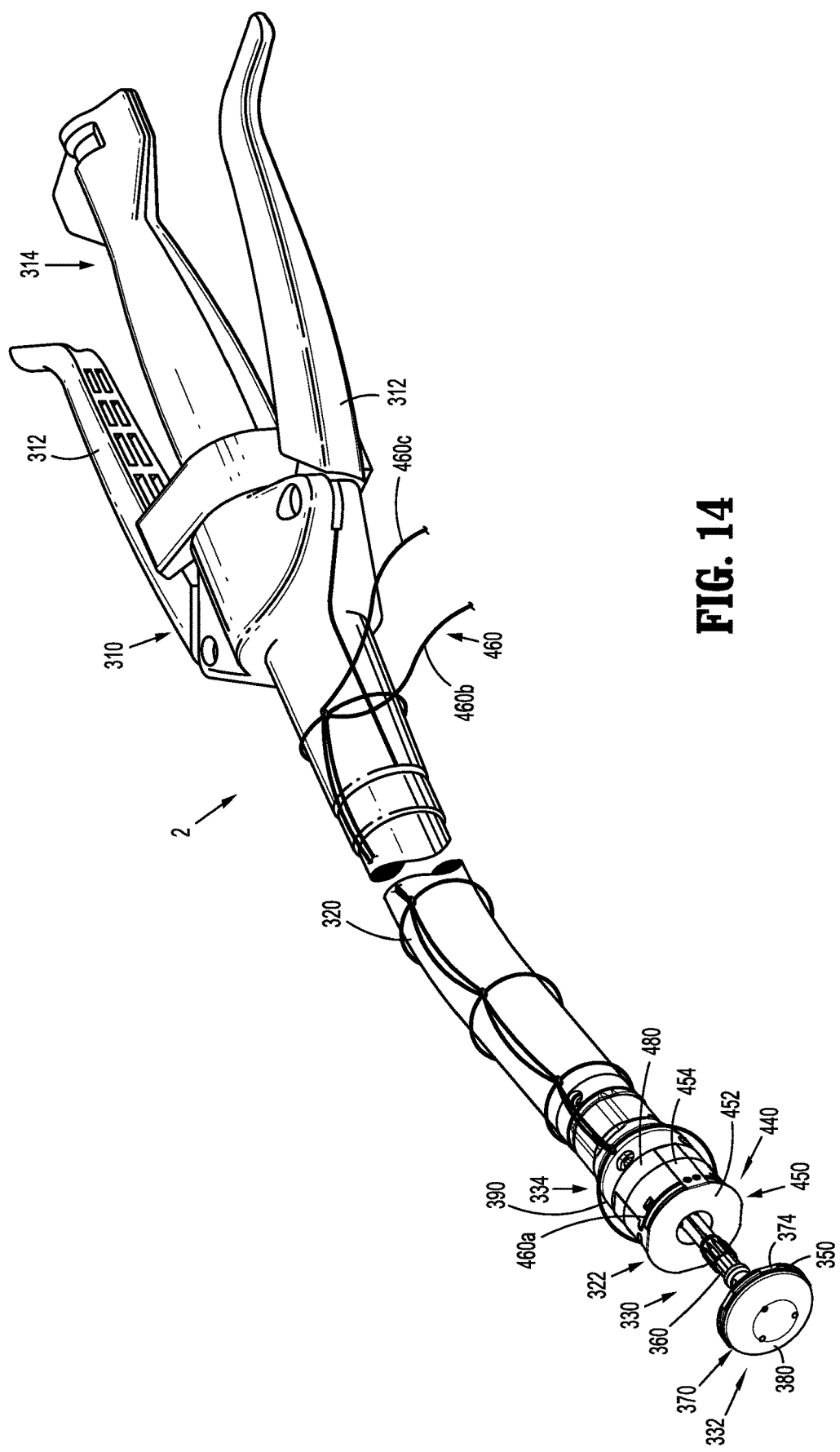
FIG. 14 is a perspective view of a surgical stapling apparatus having surgical buttresses disposed thereon in accordance with an embodiment of the present disclosure.

With reference now to FIG. 14, a surgical stapling apparatus or surgical stapler 2 in the form of an annular surgical stapling device is shown for use in stapling tissue and applying one or more buttress materials or surgical buttresses to tissue. The surgical stapler 2 generally includes a handle assembly 310, an elongate tubular body 320 extending distally from the handle assembly 310, and an end effector 330 extending distally from the elongate tubular body 320. The end effector 330 includes an anvil assembly 332 and a staple cartridge assembly 334. The anvil assembly 332 is releasably coupled to a distal end portion 322 of the elongate tubular body 320, and the staple cartridge assembly 334 is disposed at the distal end portion 322 of the elongate tubular body 320.

The handle assembly 310 includes at least one movable handle member 312 for actuating the firing of staples 410 (FIG. 18) from the staple cartridge assembly 334 and the cutting of tissue secured between the anvil and staple cartridge assemblies 332, 334. The handle assembly 310 further includes an advancing member 314 for moving the anvil assembly 332 between an open or spaced apart position and a closed or approximated position relative to the staple cartridge assembly 334.

The elongate tubular body 320 may be flexible or rigid, and/or straight or curved along a portion or the entirety thereof. It should be understood that the elongate tubular body 320 may be otherwise configured (e.g., shaped and/or dimensioned) depending on, for example, the surgical application or procedure of use as is within the purview of those skilled in the art. The staple cartridge assembly 334 may be fixedly connected to the distal end portion 322 of the elongate tubular body 320 or may be configured to concentrically fit within, or be otherwise connected to, the distal end portion 322 of the elongate tubular body 320 such that the staple cartridge assembly 334 is removable and replaceable.

For a detailed description of the structure and function of exemplary surgical stapling apparatus, reference may be made to U.S. Pat. Nos. 4,473,077; 4,576,167; 5,005,749; 5,119,983; 5,588,579; 5,915,616; and 6,053,390, the entire contents of each of which are incorporated herein by reference. It should be understood that a variety of annular surgical stapling apparatus may be utilized with the surgical buttress assemblies of the present disclosure.

Figure 15:
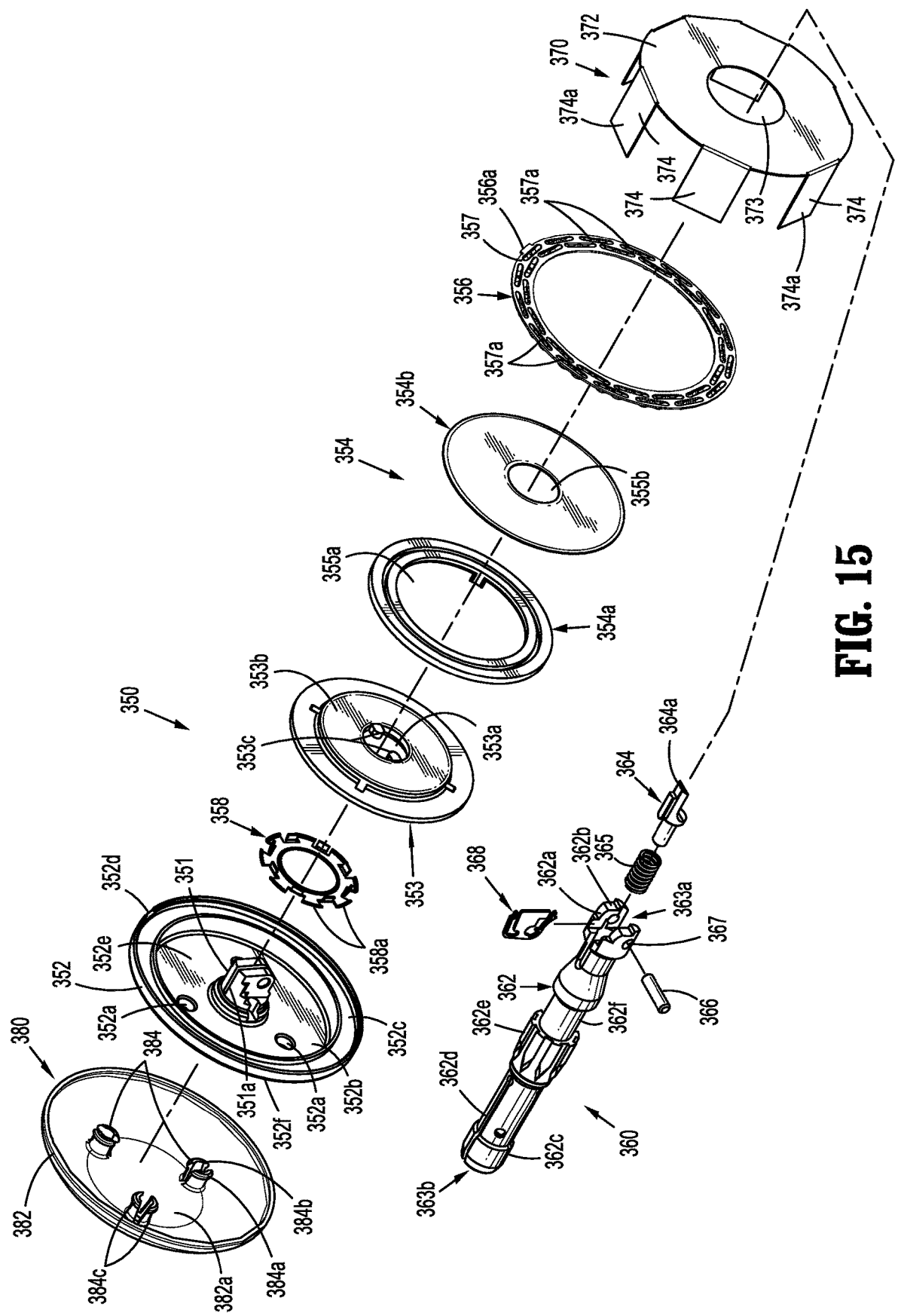
FIG. 15 is an exploded, perspective view of an anvil assembly of an end effector of the surgical stapling apparatus of FIG. 14.

As shown in FIGS. 14 and 15, the anvil assembly 332 includes a head assembly 350 and a center rod assembly 360 pivotally secured to the head assembly 350. The head assembly 350 includes a central post or connector 351, a housing or anvil head 352, a backup plate 353, a cut ring assembly 354, an anvil plate 356, and a spacer 358. The connector 351 extends proximally from the housing 352 and is dimensioned to operatively couple to a first end portion 362*a* of a center rod 362 of the center rod assembly 360. The connector 351 may be substantially centrally positioned through a bore (not shown) defined in the housing 352, or the connector 351 may be integrally or monolithically formed with the housing 352. One or more openings 352*a* (e.g., pressure relief openings) are defined through the housing 352, and the housing 352 includes an inner annular recess 352*b* and an outer annular recess 352*c* supporting the backup plate 353, the cut ring assembly 354, the anvil plate 356, and the spacer 358 therein.

The anvil plate 356 is supported in the outer annular recess 352*c* of the housing 352 and includes a tissue facing surface 357 having a plurality of staple forming pockets 357*a* for receiving and deforming staples. The anvil plate 356 may include at least one tab 356*a* extending radially outwardly form the anvil plate 356 that is received within a cutout 352*d* formed in an outer rim of the housing 352. The tab 356*a* and the cutout 352*d* function to align and/or properly locate and retain the anvil plate 356 within the outer annular recess 352*c* of the housing 352.

The inner annular recess 352*b* is located between the connector 351 and the outer annular recess 352*c*. The backup plate 353 includes a substantially centrally located opening 353*a* positioned and slidably mounted about the connector 351 within the inner annular recess 352*b*. The backup plate 353 includes a raised center platform 353*b* and a pair of inwardly extending fingers 353*c*, although other configurations are envisioned.

The cut ring assembly 354 includes a body 354*a* and a cover 354*b*. The body 354*a* includes an opening 355*a* having an inner configuration substantially the same as the platform 353*b* of the backup plate 353 to facilitate positioning of the cut ring assembly 354 about the platform 353*b*. The cover 354*b* includes a substantially centrally located opening 355*b* for receiving the connector 351 and is secured to an outwardly facing or proximal surface of the body 354*a*. The cut ring assembly 354 may be fixedly secured or otherwise fastened to the backup plate 353.

The spacer 358 is positioned in the inner annular recess 352*b* of the housing 352 between the backup plate 353 and an inner or proximally facing surface 352*e* of the housing 352. The spacer 358 is annular and may include deformable tabs 358*a* which engage a distally facing surface of the backup plate 353. The spacer 358 prevents the backup plate 353 and the cut ring assembly 354 from moving or being pushed into the inner annular recess 352*b* of the housing 352 until a predetermined force sufficient to deform the tabs 358*a* has been applied to the backup plate 353 and the cut ring assembly 354. The predetermined force may be, for example, close to but less than the force applied by an annular knife 420 (FIG. 18) of the staple cartridge assembly 334 to the cut ring assembly 354 as the surgical stapler 2 is fired. When the predetermined force is reached, e.g., during cutting of tissue, the backup plate 353 and the cut ring assembly 354 will move into the inner annular recess 352*b* of the housing 252 and compress the spacer 358. It is envisioned that other crushable, deformable, collapsible, and/or movable spacing members may be used to retain the backup plate 353 and the cut ring assembly 354 in a fixed position until the predetermined force has been applied to the backup plate 353 and the cut ring assembly 354.

In embodiments, the backup plate 353 may be omitted and the cut ring assembly 354 may be configured for positioning about the connector 351 within the housing 352 with the spacer 358 positioned in the inner annular recess 352*b* of the housing 352 between the cutting ring assembly 354 and the inner surface 352*e* of the housing 352.

The center rod assembly 360 includes a center rod or anvil shaft 362, a plunger 364, and a plunger spring 365. A pivot pin 366 pivotably secures the connector 351 of the head assembly 350 to the center rod 362 via throughbores 367 such that the head assembly 350 is pivotably mounted to the center rod assembly 360.

The plunger 364 is slidably positioned in a bore 363*a* formed in a first end portion 362*a* of the center rod 362. The plunger 364 includes an engagement finger 364*a* biased into engagement with the connector 351 by the plunger spring 365 to urge the head assembly 350 from a non-tilted or operative position to a pivoted or tilted position on the center rod 362. In a preferred position, the fingers 353*c* formed on the backup plate 353 engage a top surface 362*b* of the center rod 362 to prevent the head assembly 350 from pivoting about the pivot pin 366. When the anvil assembly 332 is attached to a surgical stapler 2 and the surgical stapler 2 is fired, the backup plate 353 and the cut ring assembly 354 are pushed into the inner annular recess 352*b* of the housing 352 about the connector 351 by the annular knife 420 (FIG. 18) to move the fingers 353*c* of the backup plate 353 out of engagement with the top surface 362*b* of the center rod 362 and to permit the plunger 364 to pivot the head assembly 350 about the pivot pin 366. The spacer 358 prevents inadvertent or premature movement of the backup plate 353 and the cut ring assembly 354 to prevent premature or inadvertent tilting of the head assembly 350.

A retaining clip 368 is positioned in a transverse slot 351*a* formed in the connector 351 and is operatively engaged with the pivot pin 366. After the backup plate 353 has been pushed into the inner annular recess 252*b* of the housing 252 by the annular knife 420 of the surgical stapler 2, the retaining clip 368 is configured to prevent the backup plate 353 and the cut ring assembly 354 from sticking to the annular knife 420 when the anvil assembly 332 is moved away from the staple cartridge assembly 334.

A second end portion 362*c* of the center rod 362 includes a bore 363*b* defined by flexible arms 362*d*. The flexible arms 362*d* are configured and dimensioned to releasably secure a trocar (not shown) of the surgical stapler 2 to the center rod 362 of the anvil assembly 332. A plurality of splines 362*e* are formed about the center rod 362 to align the anvil assembly 332 with the staple cartridge assembly 334 of the surgical stapler 2, and a recessed portion 362*f* of the center rod 362 facilitates grasping of the anvil assembly 332 by a user (e.g., with a grasper).

With continued reference to FIGS. 14 and 15, a surgical buttress 370 is releasably coupled to the anvil assembly 332 of the surgical stapler 2 via an anvil cap 380. The surgical buttress 370 may be fabricated from biocompatible materials which are bioabsorbable or non-absorbable, natural or synthetic materials, or combinations thereof, and may be porous, non-porous, or combinations thereof, as described above with respect to the surgical buttress 100, 200.

The surgical buttress 370 includes a body or buttress portion 372 and a plurality of legs 374 extending radially outwardly from the body portion 372. The body portion 372 has a generally circular or annular configuration defining a central aperture 373 therethrough. The body portion 372 is sized and dimensioned to extend over (e.g., completely cover) the tissue facing surface 357 of the anvil assembly 332. The central aperture 373 is sized and dimensioned to allow passage of the center rod 362 of the anvil assembly 332 therethrough. In embodiments, the central aperture 373 has a diameter that is larger than the diameter of the center rod 362 of the anvil assembly 332 and, in some embodiments, the central aperture 373 has a diameter that is about the same as or smaller than the diameter of the center rod 362 such that the center rod 362 frictionally engages the surgical buttress 370. The legs 374 of the surgical buttress 370 extend from the body portion 372 radially beyond the tissue facing surface 357 of the anvil assembly 332 such that the legs 374 can be wrapped around the housing 352 of the anvil assembly 332. While the legs 374 are shown extending linearly and uniformly from the body portion 372, other configurations of the legs 374 are envisioned.

The surgical buttress 370 is disposed on the anvil assembly 332 of the surgical stapler 2 with the body portion 372 selectively supported on and positioned over the tissue facing surface 357 of the anvil plate 356 and the legs 374 selectively positioned around the housing 352 such that free ends 374a of the legs 374 are adjacent an outer or distal surface 352f of the housing 352. The legs 374 are releasably secured against the distal surface 352f of the housing 352 by the anvil cap 380.

The anvil cap 380 includes a cap body 382 supported on the distal surface 352f of the housing 352. The cap body 382 includes one or more pegs 384 extending proximally from an inner or proximal wall 382a of the cap body 382. Each peg 384 has a split body including first and second legs 384a, 384b terminating at flanged ends 384c. The first and second legs 384a, 384b are deflectable inwardly and outwardly relative to each other. The pegs 384 are positionable through the openings 352a defined in the housing 352 to facilitate securement of the anvil cap 380 to the housing 352 and to permit the anvil cap 380 to move relative to the housing 352 between an approximated or closed position and an unapproximated or open position, as described in further detail below.

Figure 16:
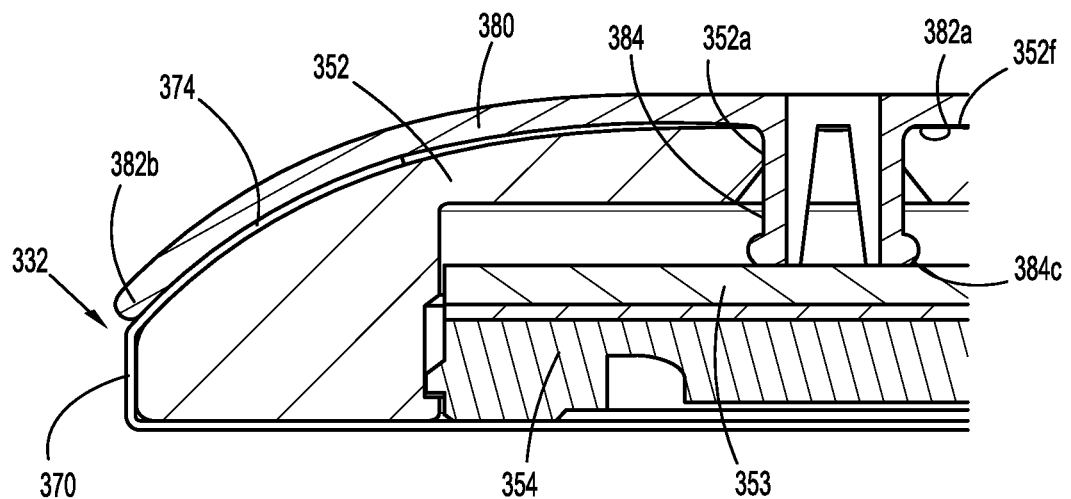
FIG. 16 is a cross-sectional, close-up view of an anvil head of the anvil assembly of FIG. 15, illustrating an anvil cap in an approximated position securing a surgical buttress to the anvil head.
Figure 17:
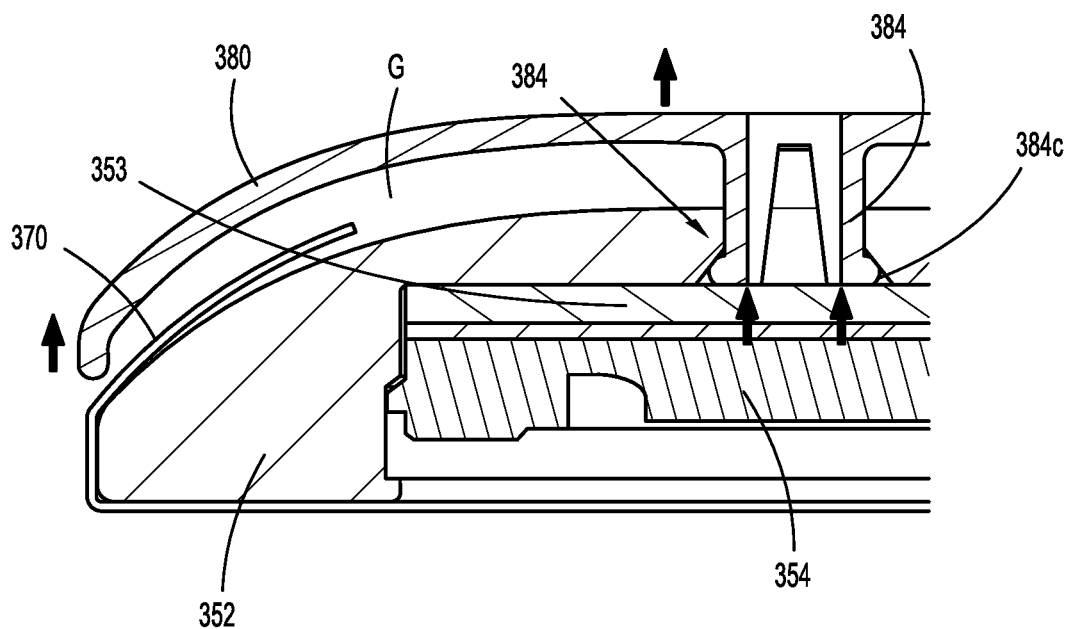
FIG. 17 is a cross-sectional, close-up view of the anvil head of FIG. 16, illustrating the anvil cap in an unapproximated position releasing the surgical buttress from the anvil head.

The anvil cap 380 is utilized to releasably attach the surgical buttress 370 to the anvil assembly 332. In the approximated position, as shown in FIG. 16, the pegs 384 of the anvil cap 380 are positioned through the openings 352a of the housing 352 of the anvil assembly 332 such that the proximal wall 382a of the anvil cap 380 abuts the distal surface 352f of the housing 352, and engages and holds the legs 374 of the surgical buttress 370 therebetween. In embodiments, the legs 374 of the surgical buttress 370 are retained between a curved rim 382b of the body 382 of the anvil cap 380 and the distal surface 352f of the housing 352. The flanged ends 384c of the pegs 384 of the anvil cap 380 are positioned adjacent to (e.g., against) the backup plate 353 of the anvil assembly 332. Upon firing of the surgical stapler 2, the cutting ring assembly 354 and the backup plate 353 are moved towards and into engagement with the pegs 384 to move the anvil cap 380 to the unapproximated position, as shown in FIG. 17. In the unapproximated position, the pegs 384 and thus, the anvil cap 380 are moved distally or axially away from the housing 352 to create a gap "G" between the housing 352 and the anvil cap 380 such that the legs 374 of the surgical buttress 370 can be released from the anvil assembly 332 and the surgical buttress 370 can separate from the anvil assembly 332. The flanged ends 384c of the pegs 384 act as self-locking features to ensure that the anvil cap 380 remains attached to, and does not pop off the housing 352 when moved between the approximated and unapproximated positions.

In a method of assembling the surgical buttress 370 to the stapler 2, the body portion 372 of the surgical buttress 370 is position adjacent to the tissue facing surface 357 of the anvil plate 356 and the legs 374 are wrapped around the housing 352 of the anvil assembly 332 such that the free ends 374a of the legs 370 of the surgical buttress 374 are positioned adjacent the distal surface 352f of the housing 352. The anvil cap 380 is then attached to the housing 352 by aligning the pegs 384 with the openings 352a defined in the housing 352 and axially pushing the anvil cap 380 towards the housing 352 and into the approximated position such that the legs 374 of the surgical buttress 370 are trapped between the anvil cap 380 and the housing 352. During movement of the anvil cap 380 towards the housing 352, the first and second legs 384a, 384b of each of the pegs 384 are deflected towards each other as the flanged ends 384c are compressed into the opening 352a of the housing 352 and then return to their biased position such that the flanged ends 384c of the pegs 384 are slidably retained within the housing 352. The anvil assembly 332, with loaded surgical buttress 370, is ready for use with the surgical stapler 2 according to methods within the purview of those skilled in the art.

Figure 18:
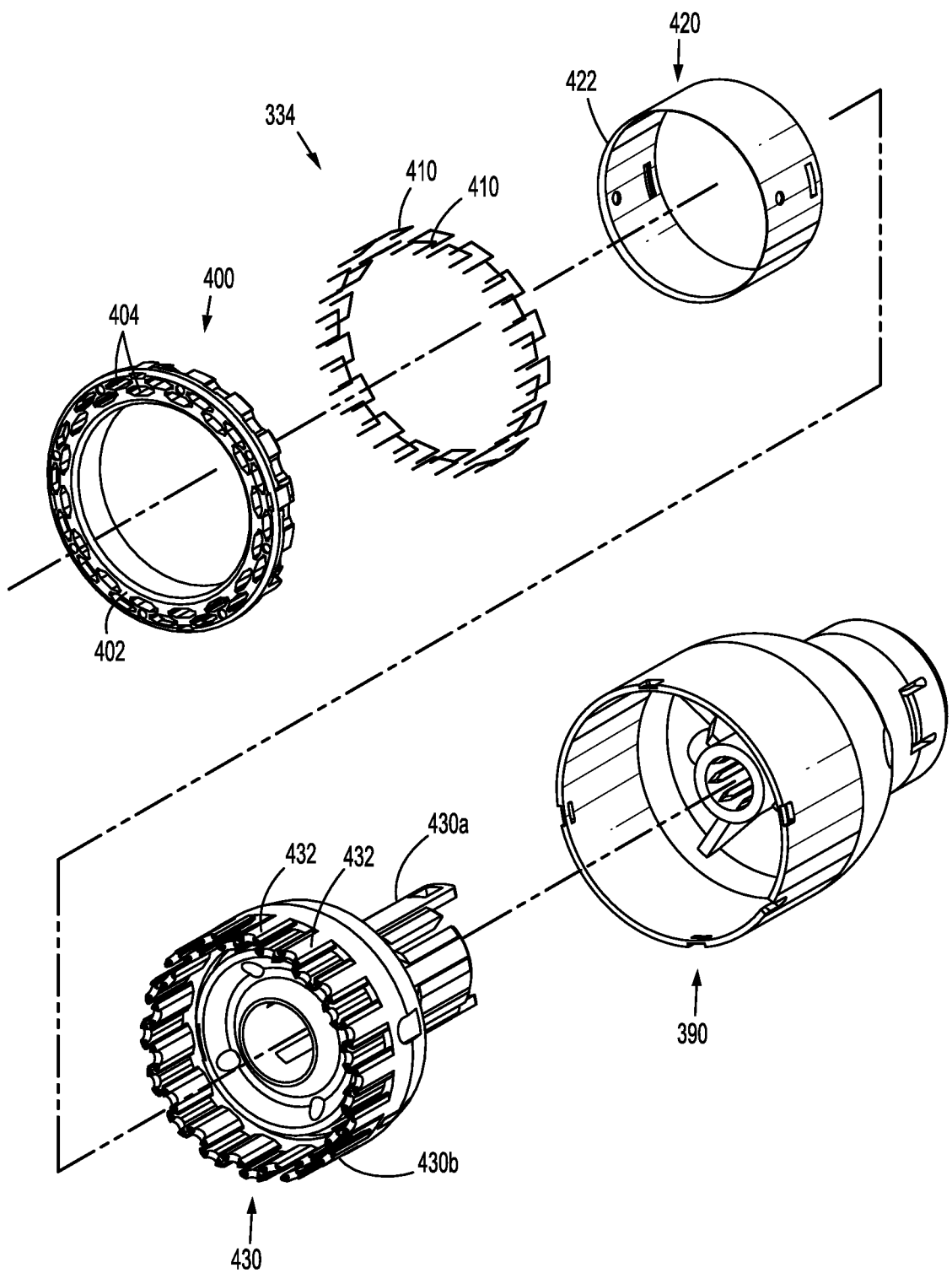
FIG. 18 is an exploded, perspective view of a staple cartridge assembly of an end effector of the surgical stapling apparatus of FIG. 14.

With reference now to FIG. 18, in conjunction with FIG. 14, the staple cartridge assembly 334 is disposed at the distal end portion 322 of the elongate tubular body 320 of the surgical stapler 2 and is configured to fire and form an annular array of surgical fasteners or staples, and to sever a ring of tissue. The staple cartridge assembly 334 includes a housing 390 having a staple guide 400, a plurality of staples 410, an annular knife 420, and a staple pusher 430 disposed therein. The staple guide 400 includes a tissue facing surface 402 defining at least one annular array of staple receiving slots 404 therein. The plurality of staples 410 are disposed, one each, in each of the staple receiving slots 404. The staple pusher 430 includes a proximal portion 430a having a generally frusto-conical shape and a distal portion 430b defining at least one concentric ring of peripherally spaced fingers 432, each of which is received within one of the respective staple receiving slots 404 of the staple guide 400. The annular knife 420 is mounted to the staple pusher 430 and is substantially in the form of an open cup with a rim thereof defining a knife edge 422. The annular knife 420 is disposed radially inward of the staples 410 and the staple receiving slots 404 of the staple guide 400 such that, in use, as the staple pusher 430 is advanced, the annular knife 420 is also advanced axially in a linear direction.

A surgical buttress assembly 440 is releasably coupled to the staple cartridge assembly 334 of the surgical stapler 2. The surgical buttress assembly 440 includes a surgical buttress 450 and an elongate member, tether or leash 460. The surgical buttress 450 may be fabricated from biocompatible materials which are bioabsorbable or non-absorbable, natural or synthetic materials, or combinations thereof, and may be porous, non-porous, or combinations thereof, as described above with respect to the surgical buttress 100, 200, 370.

Figure 19:
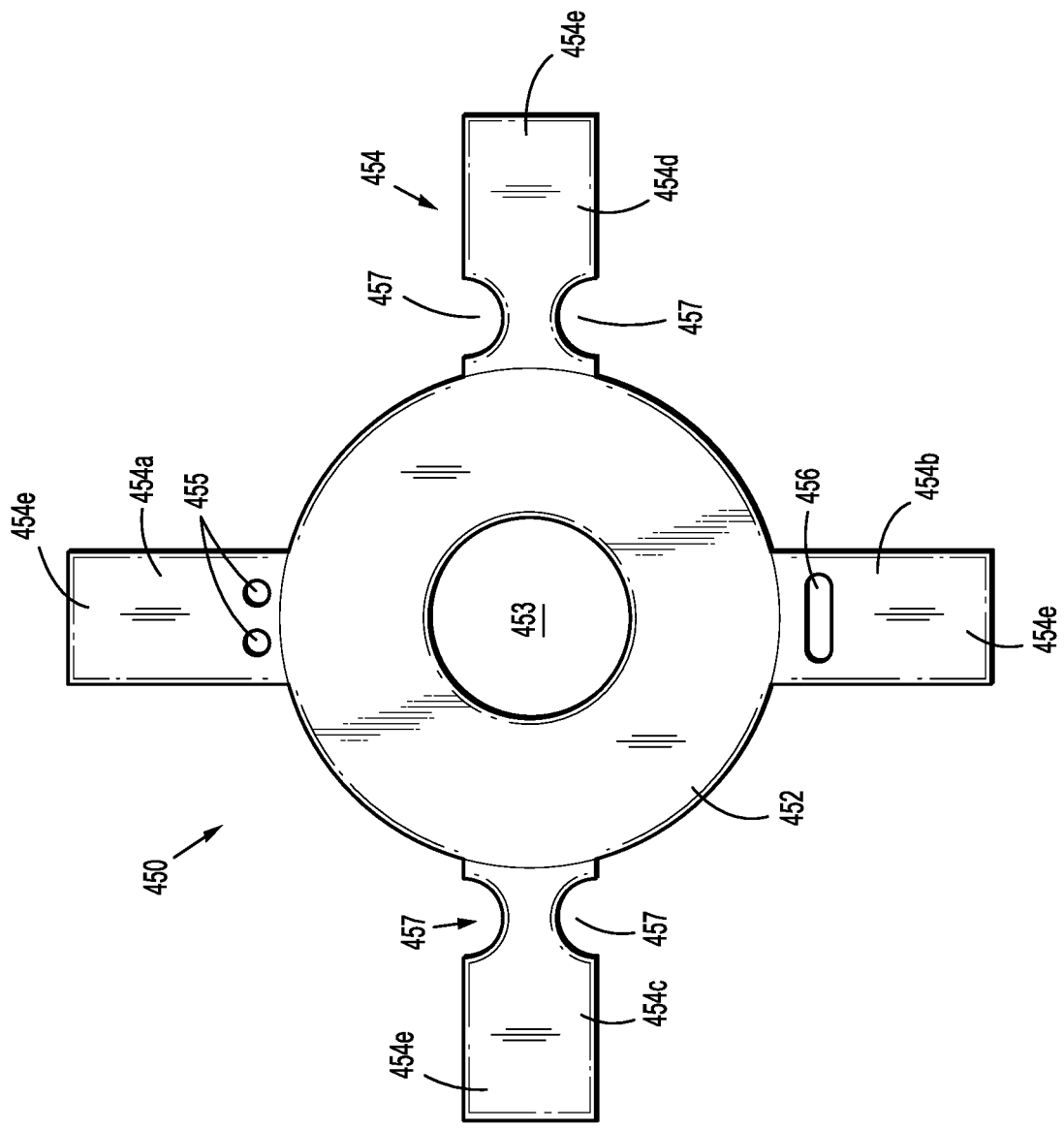
FIG. 19 is a plan view of a surgical buttress of the surgical stapling apparatus of FIG. 14 in accordance with an embodiment of the present disclosure.

As seen in FIGS. 14 and 19, the surgical buttress 450 is substantially the same as surgical buttress 370 and includes a body or buttress portion 452 and a plurality of legs 454 extending radially outwardly from the body 452. The body 452 has a generally circular or annular configuration defining a central aperture 453 therethrough. The body 452 is sized and dimensioned to extend over (e.g., completely cover) the tissue facing surface 402 of the staple cartridge assembly 334. The central aperture 453 is sized and dimensioned to allow passage of the center rod 362 of the anvil assembly 332 therethrough. The legs 454 of the surgical buttress 450 extend from the body 452 radially beyond the tissue facing surface 402 of the staple cartridge assembly 334. Together, the body 452 and the legs 454 are sized and shaped to be positioned over the staple cartridge assembly 334.

The elongate member 460 is secured to the legs 454 of the surgical buttress 450 and extends proximally therefrom. The elongate member 460 is of a sufficient length to be accessible outside of a patient's body and may extend the length of the elongate tubular body 320 of the surgical stapler 2 (e.g., at least to or beyond the handle assembly 310). As seen in FIG. 14, the elongate member 460 may be wrapped or loosely tied along the length of the elongate tubular body 320, or the elongate member 460 may extend freely along the length thereof. The elongate member 460 may be a band, a cord, a rope, a strap, a suture, among other elongate structures tethered to the legs 454 of the surgical buttress 450.

As shown in FIG. 19, the legs 454 of the surgical buttress 450 are disposed equidistantly around the body 452. Each of the legs 374 is configured to include at least one opening or cutout disposed in a portion of the leg 454 adjacent the body 452 that will be aligned with the elongate member 460 (FIG. 14). For example, a first leg 454a includes a pair of openings 455 defined therein, a second leg 454b disposed in opposed relation relative to the first leg 454a defines an elongated opening or slot 456 therein, and third and fourth legs 454c, 454d each include a pair of opposed cutouts 457 (e.g., recesses or notches) defined therein.

With reference again to FIGS. 14 and 19, a central portion 460a of the elongate member 460 is looped through the pair of openings 455 defined in the second leg 454a, and first and second elongated portions 460b, 460c of the elongate member 460 are passed under the second and third legs 454c, 454d, respectively, such that the elongate member 460 is aligned with and positioned beneath the opposed cutouts 457 defined in the third and fourth legs 454c, 454d. The first and second elongated portions 460b, 460c are then passed through the elongated opening 456 of the second leg 454b and guided proximally along the elongate tubular body 320 of the surgical stapler 2. In embodiments, a sleeve tube 480 is utilized to hold free ends 454e of the legs 454 against the housing 390 of the staple cartridge assembly 334. Alternatively, the free ends 454e of the legs 454 may be secured to the staple cartridge assembly 334 via any suitable attachment features within the purview of those skilled in the art, such as, mechanical attachment features (e.g., sutures, pins), chemical attachment features (e.g., adhesives), and/or attachment methods (e.g., welding).

Figure 20:
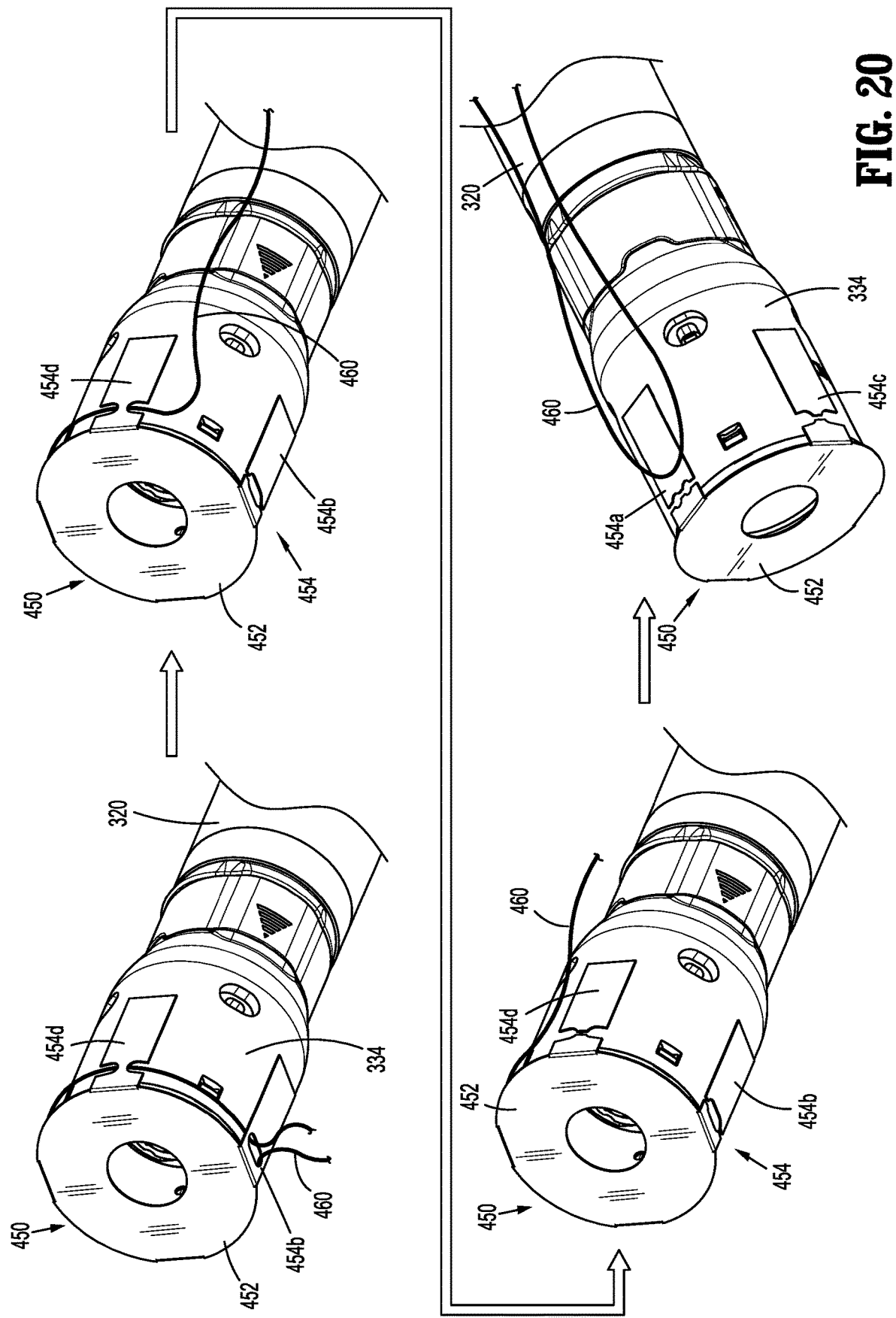
FIG. 20 is a perspective view of a staple cartridge assembly of the surgical stapling apparatus of FIG. 14 including the surgical buttress of FIG. 19 and a leash, illustrating a step-by-step release of the surgical buttress from the staple cartridge assembly in accordance with an embodiment of the present disclosure.

When the elongate member 460 is pulled away from the elongate tubular body 320 (e.g., proximally towards a user), the elongate member 460 breaks (e.g., cuts or tears) through the legs 454 of the surgical buttress 450 as shown in FIG. 20. From an initial stage, the elongate member 460 first tears through the second leg 454b of the surgical buttress 450, then through the third and fourth legs 454c, 454d, and finally through the first leg 454a thus separating the legs 454 from the body 452 so that the body 452 is free and the legs 454 remain secured to the staple cartridge assembly 334. Other configurations of the legs 454 of the surgical buttress 450 are also envisioned that are suitable for separating the legs 454 from the body 452 of the surgical buttress 450 (e.g., weakened, perforated, and/or thinner regions of the legs) via the elongate member 460.

In a method of use, the loaded surgical stapler 2 is introduced to a surgical site. Specifically, the surgical stapler 2 and detachable anvil assembly 332 are used in an anastomosis procedure to effect joining of tissue sections (e.g., intestinal or other tubular organ sections). The surgical stapler 2 is operated within methods known by those skilled in the art. Once the anvil and staple cartridge assemblies 332, 334 are positioned in the tissue sections and the anvil assembly 332 has been connected to the elongated tubular body 320 of the surgical stapler 2, the anvil assembly 332 is approximated towards the elongated tubular body 320 (e.g., via the advancing member 314 of the handle assembly 310) to approximate the tissue sections and the surgical stapler 2 is fired (e.g., via movable handle members 312) to fire the staples 410 from the staple cartridge assembly 334 towards the housing 352 of the anvil assembly 332 to effect stapling of the tissue sections to one another, as well as the surgical buttresses 370, 450 to the tissue sections. During firing, the annular knife 420 cuts the stapled tissue sections, as well as any portion of the surgical buttresses 370, 450 extending radially inwardly of the annular knife 420 to complete the anastomosis.

During actuation of the surgical stapler 2, the cut ring assembly 334 is pushed axially such that the anvil cap 380 is moved distally away from the anvil assembly 332 from the approximated position to the unapproximated position, as described above, so that the legs 374 of the surgical buttress 370 associated with the anvil assembly 332 are free to release the now-stapled surgical buttress 370 therefrom. The surgical buttress 450 associated with the staple cartridge assembly 334 can then be detached from the now-stapled body 452 of the surgical buttress 450 by pulling the elongate member 460 proximally to separate the legs 454 from the body 452, as described above.

In any of the embodiments disclosed herein, the surgical buttress can include, or be used with, brachytherapy, chemotherapy, other medical materials or pharmaceuticals. The buttress portion or body of the surgical buttress can have pockets, apertures, or other features for retaining brachytherapy seeds with the buttress portion, or brachytherapy seeds or materials can be incorporated into a suture or sutures that are threaded into or through the buttress portion or otherwise attached thereto. A coating having brachytherapy materials can be applied to a buttress portion or body of a surgical buttress by spraying or dipping. Chemotherapy pharmaceuticals or agents can be incorporated into the buttress portion of the surgical buttress, coated thereon, or applied as part of a suture or suture or other feature.

It should be understood that the surgical buttresses, surgical buttress loading assemblies, and/or surgical buttress assemblies described herein may be used with other surgical apparatus, such as electromechanical surgical devices as described, for example, in U.S. Patent Appl. Pub. Nos. 2015/0157320 and 2015/0157321, and U.S. patent application Ser. No. 15/972,606, filed on May 7, 2018, the entire contents of each of which are incorporated herein by reference.

Figure 21:
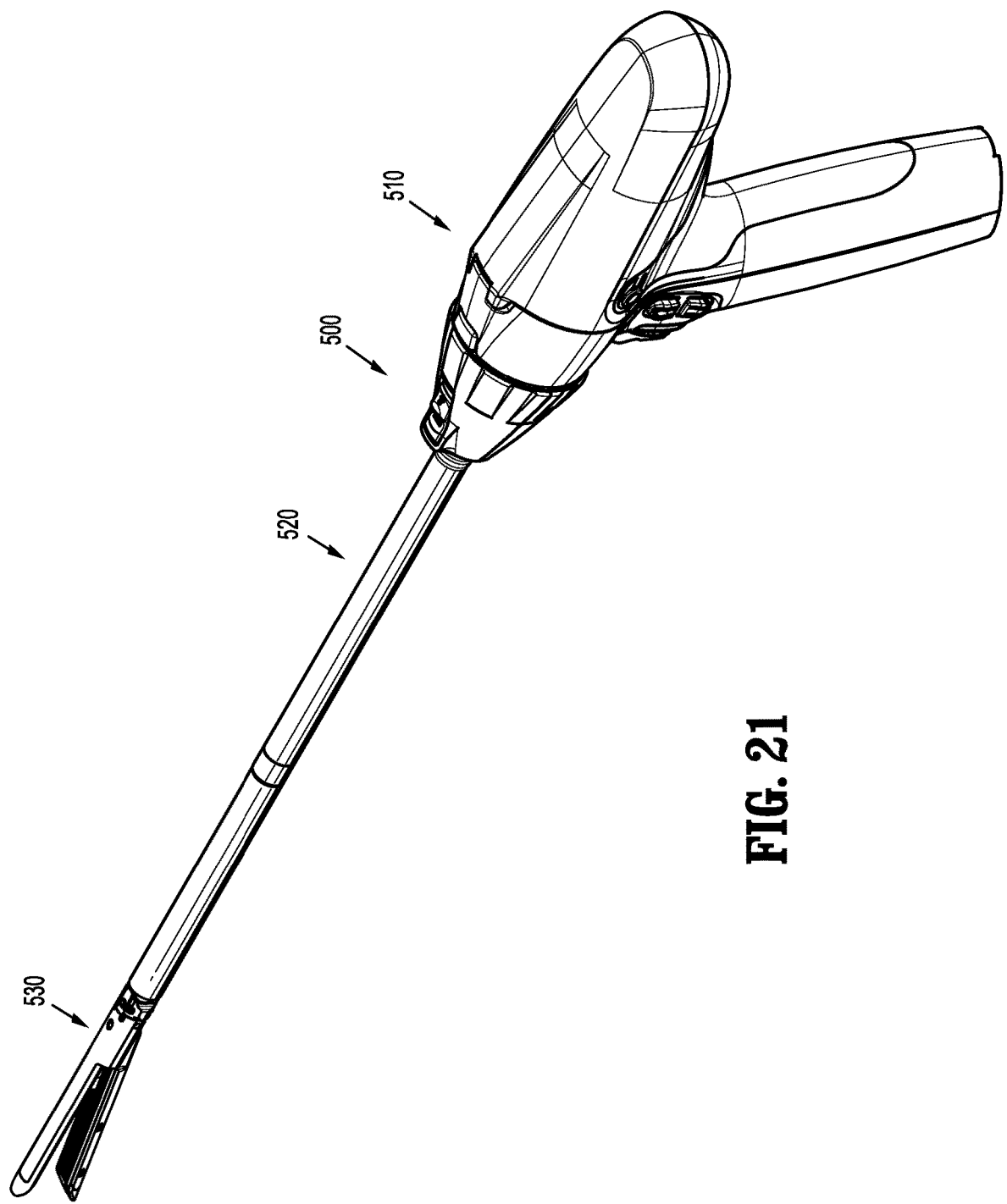
FIG. 21 is a perspective view of a surgical stapling apparatus in accordance with another embodiment of the present disclosure.

For example, as shown in FIG. 21, a surgical device 500 is in the form of a powered handheld electromechanical instrument. The surgical device 500 includes a handle assembly 510 configured for selective connection with an adapter assembly 520 and, in turn, the adapter assembly 200 is configured for selective connection with an end effector

Figure 22:
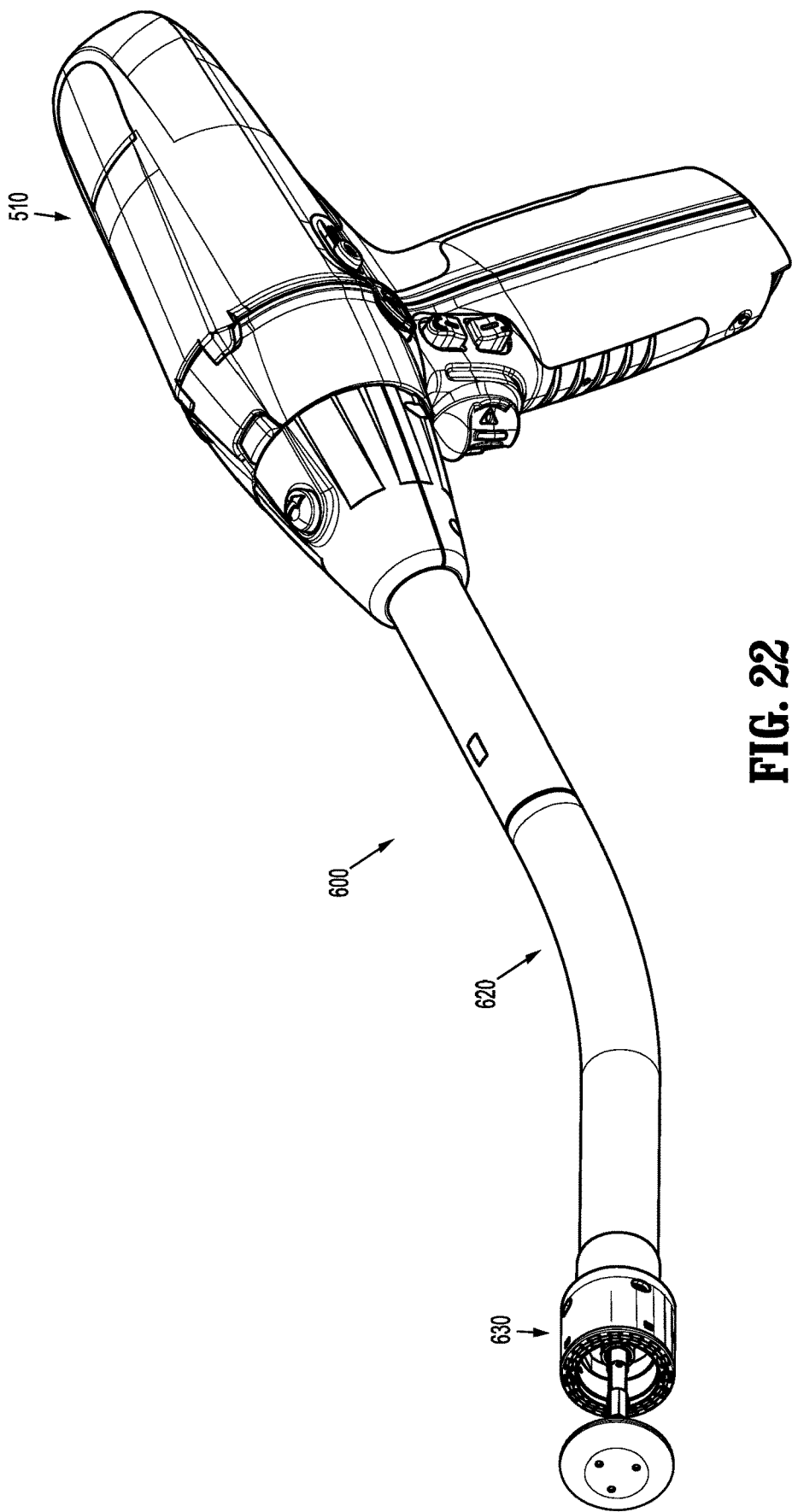
FIG. 22 is a perspective view of a surgical stapling apparatus in accordance with yet another embodiment of the present disclosure.

530. Surgical buttresses 100, 100*a*, 100*b* and/or surgical buttress loading assembly 201 may be configured for use with the end effector 530 of the surgical device 500. As another example, as shown in FIG. 22, a surgical device 600, also in the form of a powered handheld electromechanical instrument, includes the handle assembly 510 configured for selective connection with an adapter assembly 620 and, in turn, the adapter assembly 620 is configured for selective connection with an end effector 630. Surgical buttress assemblies including the surgical buttress 370 and the anvil cap 380, and/or the surgical buttress 450 and the elongate member 460 may be configured for use with the end effector 630 of the surgical device 600.

While several embodiments of the disclosure have been shown in the drawings, it is not intended that the disclosure be limited thereto, as it is intended that the disclosure be as broad in scope as the art will allow and that the specification be read likewise. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Therefore, the above description should not be construed as limiting, but merely as exemplifications of preferred embodiments. Thus the scope of the embodiments should be determined by the appended claims and their legal equivalents, rather than by the examples given.

What is claimed is:

1. A surgical buttress loading assembly for use with a surgical stapling apparatus, comprising:
   a surgical buttress including a tubular body and an elongate member extending from the tubular body; and
   a surgical buttress applicator including a base and a handle releasably engaged with the base, the handle configured to releasably engage an elongate tubular body portion of the surgical stapling apparatus when separated from the base, the tubular body of the surgical buttress positioned within a cavity of the base, the elongate member of the surgical buttress disposed within and extending through the handle.

2. The surgical buttress loading assembly according to claim 1, wherein the base of the surgical buttress applicator includes an elongate body having a proximal end defining an opening into the cavity, and a closed distal end.

3. The surgical buttress loading assembly according to claim 2, wherein a tab extends proximally from the proximal end of the elongate body of the base and between the handle and the cavity of the base, the tab positioned through an aperture defined in the elongate member of the surgical buttress.

4. The surgical buttress loading assembly according to claim 2, wherein a tab extends proximally from the proximal end of the elongate body of the base, the tab being positionable through an aperture defined in the tubular body of the surgical buttress.

5. The surgical buttress loading assembly according to claim 1, wherein the base of the surgical buttress applicator includes a fin having a concave wall defining an arcuate cut-out configured to receive the handle therein.

6. The surgical buttress loading assembly according to claim 5, wherein the handle includes an outer wall defining a groove therein that is configured to receive the concave wall of the base therein to releasably retain the handle within the arcuate cut-out of the base.

7. The surgical buttress loading assembly according to claim 1, wherein the handle of the surgical buttress applicator includes an outer handle housing including an outer wall and an inner wall defining an annular cavity therebetween, the elongate member of the surgical buttress disposed within the annular cavity of the outer handle housing.

8. The surgical buttress loading assembly according to claim 7, wherein the outer wall of the outer handle housing includes a slot defined therethrough that is in fluid communication with the annular cavity, the elongate member of the surgical buttress extending through the slot.

9. The surgical buttress loading assembly according to claim 7, wherein the handle of the surgical buttress application includes an inner handle housing rotatably disposed within the annular cavity of the outer handle housing, the elongate member of the surgical buttress wrapped around the inner handle housing.

10. The surgical buttress loading assembly according to claim 9, wherein the inner wall of the outer handle housing includes flexible wall segments extending radially around a central opening defined in the outer handle housing.

11. The surgical buttress loading assembly according to claim 10, wherein at least one of the flexible wall segments includes a lip extending therefrom to aid in retaining the inner handle housing within the annular cavity of the outer handle housing.

12. The surgical buttress loading assembly according to claim 9, wherein the inner handle housing includes an annular base including an inner surface configured to engage and be rotatably mounted on the inner wall of the outer handle housing.

13. The surgical buttress loading assembly according to claim 12, wherein the inner handle housing includes annular flanges extending from opposed sides of the annular base to aid in retaining the elongate member of the surgical buttress on an outer surface of the annular base.

14. The surgical buttress loading assembly according to claim 1, wherein a terminal end of the elongate member of the surgical buttress is secured within the handle.

15. A surgical stapling system comprising:
    a surgical stapling apparatus including:
      a handle assembly;
      an elongate tubular body portion extending distally from the handle assembly; and
      an end effector extending distally from the elongate tubular body portion, the end effector including an anvil assembly and a staple cartridge assembly; and
    a surgical buttress loading assembly including:
      a surgical buttress including a tubular body and an elongate member extending from the tubular body; and
      a surgical buttress applicator including a base and a handle releasably engaged with the base, the handle configured to releasably engage the elongate tubular body portion of the surgical stapling apparatus, the elongate member of the surgical buttress disposed within and extending through the handle, and the tubular body of the surgical buttress positioned within a cavity of the base, the cavity of the base sized and shaped to slidably receive at least one of the anvil assembly or the staple cartridge assembly of the surgical stapling apparatus therein.

16. The surgical stapling system according to claim 15, wherein the tubular body of the surgical buttress includes a buttress portion and a folded portion, and the base of the surgical buttress applicator includes a first wall portion configured to extend over a tissue facing surface of the anvil or staple cartridge assembly and a second wall portion configured to extend around the anvil or staple cartridge assembly and over an outwardly facing surface of the anvil or staple cartridge assembly, the buttress portion of the surgical buttress positioned adjacent to the first wall portion and the folded portion positioned adjacent to the second wall portion such that the tubular body of the surgical buttress is open to receive the anvil or staple cartridge assembly therein.

17. The surgical stapling system according to claim 15, wherein the handle of the surgical buttress applicator includes a pair of fingers extending from an outer wall thereof, the pair of fingers configured to releasably engage the elongate tubular body portion of the surgical stapling apparatus.

18. A method of using a surgical buttress loading assembly with a surgical stapling apparatus comprising:
   sliding a surgical buttress loading assembly onto an anvil assembly or a staple cartridge assembly of a surgical stapling apparatus to position the anvil or staple cartridge assembly within a tubular body of a surgical buttress, the surgical buttress loading assembly including:
      the surgical buttress including the tubular body and an elongate member extending from the tubular body; and
      a surgical buttress applicator including a base and a handle releasably engaged with the base, the elongate member of the surgical buttress disposed within and extending through the handle, and the tubular body of the surgical buttress positioned within a cavity of the base;
   detaching the handle of the surgical buttress applicator from the base; and
   attaching the handle of the surgical buttress applicator to the elongate tubular body portion of the surgical stapling apparatus.

19. The method according to claim 18, further comprising sliding the base of the surgical buttress applicator off of the anvil or staple cartridge assembly, leaving the tubular body of the surgical buttress disposed over the anvil or staple cartridge assembly.

20. The method according to claim 19, further comprising:
   firing the surgical stapling apparatus to drive fasteners through a buttress portion of the tubular body of the surgical buttress; and
   pulling the handle of the surgical buttress applicator away from the buttress portion to separate the elongate member and a folded portion of the tubular body of the surgical buttress from the buttress portion.

* * * * *